United States Patent
Jackels et al.

(10) Patent No.: US 9,492,328 B2
(45) Date of Patent: *Nov. 15, 2016

(54) METHOD AND APPARATUS FOR MAKING ABSORBENT STRUCTURES WITH ABSORBENT MATERIAL

(71) Applicant: The Procter & Gamble Company, Cincinnati, OH (US)

(72) Inventors: Hans Adolf Jackels, Mechernich (DE); Carsten Heinrich Kreuzer, Hofheim (DE)

(73) Assignee: The Procter & Gamble Company, Cincinnati, OH (US)

(*) Notice: Subject to any disclaimer, the term of this patent is extended or adjusted under 35 U.S.C. 154(b) by 478 days.

This patent is subject to a terminal disclaimer.

(21) Appl. No.: 14/043,931

(22) Filed: Oct. 2, 2013

(65) Prior Publication Data

US 2014/0027066 A1 Jan. 30, 2014

Related U.S. Application Data

(63) Continuation of application No. 13/491,936, filed on Jun. 8, 2012, now Pat. No. 8,568,566.

(30) Foreign Application Priority Data

Jun. 10, 2011 (EP) .................................. 11169396

(51) Int. Cl.
*D21F 11/08* (2006.01)
*D21H 27/30* (2006.01)
(Continued)

(52) U.S. Cl.
CPC ... *A61F 13/00987* (2013.01); *A61F 13/15617* (2013.01); *A61F 13/15658* (2013.01);
(Continued)

(58) Field of Classification Search
CPC .................... A61F 13/15577; A61F 13/15617; A61F 13/15642; A61F 13/15658;
(Continued)

(56) References Cited

U.S. PATENT DOCUMENTS

| 1,733,997 A | 10/1929 | Marr |
| 1,734,499 A | 11/1929 | Marinsky |

(Continued)

FOREIGN PATENT DOCUMENTS

| CA | 2001370 | 4/1990 |
| CA | 2291997 | 6/2000 |

(Continued)

OTHER PUBLICATIONS

European Search Report, EP11169396.6, dated Oct. 21, 2011, 9 pages.

(Continued)

*Primary Examiner* — Eric Hug
(74) *Attorney, Agent, or Firm* — Charles R. Matson

(57) ABSTRACT

Apparatus and method for producing absorbent structures with absorbent layers with channel(s) without absorbent material, using a first moving endless surface with specific raised strip(s) and a second moving endless surface with specific mating strip(s).

8 Claims, 5 Drawing Sheets

(51) Int. Cl.

| | | |
|---|---|---|
| A61F 13/15 | (2006.01) | |
| B31F 1/07 | (2006.01) | |
| D21F 11/00 | (2006.01) | |
| A61F 13/00 | (2006.01) | |
| A61F 13/47 | (2006.01) | |
| A61F 13/49 | (2006.01) | |
| A61F 13/532 | (2006.01) | |

(52) U.S. Cl.
CPC ... *A61F 13/15764* (2013.01); *A61F 13/15804* (2013.01); *A61F 13/4704* (2013.01); *A61F 13/49001* (2013.01); *A61F 13/532* (2013.01); *D21F 11/006* (2013.01); *D21F 11/08* (2013.01); *A61F 2013/15821* (2013.01); *A61F 2013/15926* (2013.01); *B31F 1/07* (2013.01); *Y10T 156/17* (2015.01)

(58) Field of Classification Search
CPC ............ A61F 2013/15821; A61F 2013/15926; B31F 1/07; B31F 1/20; B31F 2201/07; B32B 37/00; D04H 1/70; D21F 9/00; D21F 11/00; D21F 11/006; D21F 11/008; D21F 11/04; D21F 11/08; D21F 11/12; D21F 11/14; D21H 27/002; D21H 27/02; D21H 27/30; D21H 27/38; D21H 27/40; D21H 27/42; D21J 3/00
USPC ....... 162/116, 117, 296, 297, 361, 362, 409, 162/390, 397, 398, 408, 416; 156/62.2, 156/196, 199, 209, 210; 264/119; 425/115, 425/224, 335, 336, 362, 363, 385, 394, 395, 425/406, 447; 604/374, 375
See application file for complete search history.

(56) References Cited

U.S. PATENT DOCUMENTS

| | | | |
|---|---|---|---|
| 1,989,283 A | 1/1935 | Limacher | |
| 2,058,509 A | 10/1936 | Rose | |
| 2,271,676 A | 2/1942 | Bjornbak | |
| 2,450,789 A | 10/1948 | Frieman | |
| 2,508,811 A | 5/1950 | Best et al. | |
| 2,568,910 A | 9/1951 | Condylis | |
| 2,570,796 A | 10/1951 | Gross | |
| 2,570,963 A | 10/1951 | Mesmer | |
| 2,583,553 A | 1/1952 | Faure | |
| 2,668,786 A * | 2/1954 | Swope ................ | B29C 53/285 162/116 |
| 2,705,957 A | 4/1955 | Mauro | |
| 2,714,340 A * | 8/1955 | Paul | |
| 2,788,003 A | 4/1957 | Morin | |
| 2,788,786 A | 4/1957 | Dexter | |
| 2,798,489 A | 7/1957 | Behrman | |
| 2,807,263 A | 9/1957 | Newton | |
| 2,830,589 A | 4/1958 | Doner | |
| 2,890,700 A | 6/1959 | Lönberg-Holm | |
| 2,890,701 A | 6/1959 | Weinman | |
| 2,898,912 A | 8/1959 | Adams | |
| 2,931,361 A | 4/1960 | Sostsrin | |
| 2,977,957 A | 4/1961 | Clyne | |
| 3,034,180 A * | 5/1962 | Greiner ................ | D04H 1/70 162/114 |
| 3,071,138 A | 1/1963 | Gustavo | |
| 3,150,416 A * | 9/1964 | Such ........ | D04H 1/70 162/114 |
| 3,180,335 A | 4/1965 | Duncan et al. | |
| 3,190,791 A * | 6/1965 | Potter .................. | D21J 7/00 162/217 |
| 3,207,158 A | 9/1965 | Yoshitake et al. | |
| 3,386,442 A | 6/1968 | Sabee | |
| 3,561,446 A | 2/1971 | Jones | |
| 3,572,342 A | 3/1971 | Lindquist et al. | |
| 3,572,432 A | 3/1971 | Burton | |
| 3,575,174 A | 4/1971 | Mogor | |
| 3,578,155 A | 5/1971 | Small et al. | |
| 3,606,887 A | 9/1971 | Roeder | |
| 3,610,244 A | 10/1971 | Jones | |
| 3,618,608 A | 11/1971 | Brink | |
| 3,642,001 A | 2/1972 | Sabee | |
| 3,653,381 A | 4/1972 | Warnken | |
| 3,670,731 A | 6/1972 | Harmon | |
| 3,688,767 A | 9/1972 | Goldstein | |
| 3,710,797 A | 1/1973 | Marsan | |
| 3,720,578 A * | 3/1973 | Heling ................ | B30B 9/20 162/116 |
| 3,731,688 A | 5/1973 | Litt et al. | |
| 3,756,878 A | 9/1973 | Willot | |
| 3,774,241 A | 11/1973 | Zerkle | |
| 3,776,233 A | 12/1973 | Schaar | |
| 3,814,100 A | 6/1974 | Nystrand et al. | |
| 3,828,784 A | 8/1974 | Zoephel | |
| 3,840,418 A | 10/1974 | Sabee | |
| 3,847,702 A | 11/1974 | Jones | |
| 3,848,594 A | 11/1974 | Buell | |
| 3,848,595 A | 11/1974 | Endres | |
| 3,848,597 A | 11/1974 | Endres | |
| 3,860,003 A | 1/1975 | Buell | |
| 3,863,637 A | 2/1975 | MacDonald et al. | |
| 3,882,870 A | 5/1975 | Hathaway | |
| 3,884,234 A | 5/1975 | Taylor | |
| 3,900,032 A | 8/1975 | Heurlen | |
| 3,911,173 A | 10/1975 | Sprague, Jr. | |
| 3,920,017 A | 11/1975 | Karami | |
| 3,924,626 A | 12/1975 | Lee et al. | |
| 3,926,189 A | 12/1975 | Taylor | |
| 3,929,134 A | 12/1975 | Karami | |
| 3,929,135 A | 12/1975 | Thompson | |
| 3,930,501 A | 1/1976 | Schaar | |
| 3,938,523 A | 2/1976 | Gilliland et al. | |
| 3,968,799 A | 7/1976 | Schrading | |
| 3,978,861 A | 9/1976 | Schaar | |
| 3,981,306 A | 9/1976 | Krusko | |
| 3,987,794 A | 10/1976 | Schaar | |
| 3,995,637 A | 12/1976 | Schaar | |
| 3,995,640 A | 12/1976 | Schaar | |
| 3,999,547 A | 12/1976 | Hernandez | |
| 4,014,338 A | 3/1977 | Schaar | |
| 4,034,760 A | 7/1977 | Amirsakis | |
| 4,055,180 A | 10/1977 | Karami | |
| 4,074,508 A | 2/1978 | Reid | |
| 4,084,592 A | 4/1978 | Tritsch | |
| 4,100,922 A | 7/1978 | Hernandez | |
| 4,232,674 A | 11/1980 | Melican | |
| 4,257,418 A | 3/1981 | Hessner | |
| 4,259,220 A | 3/1981 | Bunnelle et al. | |
| 4,296,750 A | 10/1981 | Woon et al. | |
| 4,315,508 A | 2/1982 | Bolick | |
| 4,324,246 A | 4/1982 | Mullane et al. | |
| 4,340,706 A | 7/1982 | Obayashi et al. | |
| 4,341,216 A | 7/1982 | Obenour | |
| 4,342,314 A | 8/1982 | Radel et al. | |
| 4,381,783 A | 5/1983 | Elias | |
| 4,388,075 A | 6/1983 | Mesek et al. | |
| 4,461,621 A | 7/1984 | Karami et al. | |
| 4,463,045 A | 7/1984 | Ahr et al. | |
| 4,469,710 A | 9/1984 | Rielley et al. | |
| 4,475,912 A | 10/1984 | Coates | |
| 4,490,148 A | 12/1984 | Beckeström | |
| 4,507,438 A | 3/1985 | Obayashi et al. | |
| 4,515,595 A | 5/1985 | Kievit et al. | |
| 4,527,990 A | 7/1985 | Sigl | |
| 4,541,871 A | 9/1985 | Obayashi et al. | |
| 4,573,986 A | 3/1986 | Minetola et al. | |
| 4,578,072 A | 3/1986 | Lancaster | |
| 4,585,448 A | 4/1986 | Enloe | |
| 4,585,450 A | 4/1986 | Rosch et al. | |
| 4,589,878 A | 5/1986 | Mitrani | |
| 4,596,568 A | 6/1986 | Flug | |
| 4,601,717 A | 7/1986 | Blevins | |
| 4,606,964 A | 8/1986 | Wideman | |

(56) References Cited

U.S. PATENT DOCUMENTS

| | | |
|---|---|---|
| 4,609,518 A | 9/1986 | Curro et al. |
| 4,610,678 A | 9/1986 | Weisman et al. |
| 4,623,342 A | 11/1986 | Ito et al. |
| 4,624,666 A | 11/1986 | Derossett et al. |
| 4,629,643 A | 12/1986 | Curro et al. |
| 4,636,207 A | 1/1987 | Buell |
| 4,641,381 A | 2/1987 | Heran et al. |
| 4,662,875 A | 5/1987 | Hirotsu et al. |
| 4,666,983 A | 5/1987 | Tsubakimoto et al. |
| 4,670,011 A | 6/1987 | Mesek |
| 4,670,012 A | 6/1987 | Johnson |
| 4,680,030 A | 7/1987 | Coates et al. |
| 4,681,579 A | 7/1987 | Toussant et al. |
| 4,681,581 A | 7/1987 | Coates |
| 4,681,793 A | 7/1987 | Linman et al. |
| 4,690,680 A | 9/1987 | Higgins |
| 4,695,278 A | 9/1987 | Lawson |
| 4,699,622 A | 10/1987 | Toussant et al. |
| 4,704,115 A | 11/1987 | Buell |
| 4,704,116 A | 11/1987 | Enloe |
| 4,710,189 A | 12/1987 | Lash |
| 4,731,066 A | 3/1988 | Korpman |
| 4,731,070 A | 3/1988 | Koci |
| RE32,649 E | 4/1988 | Brandt et al. |
| 4,747,846 A | 5/1988 | Boland et al. |
| 4,773,905 A | 9/1988 | Molee |
| 4,784,892 A | 11/1988 | Storey et al. |
| 4,785,996 A | 11/1988 | Ziecker et al. |
| 4,787,896 A | 11/1988 | Houghton et al. |
| 4,795,454 A | 1/1989 | Dragoo |
| 4,802,884 A | 2/1989 | Fröidh et al. |
| 4,808,178 A | 2/1989 | Kielpikowski |
| 4,834,735 A | 5/1989 | Alemany et al. |
| 4,834,740 A | 5/1989 | Suzuki et al. |
| 4,834,742 A | 5/1989 | Wilson et al. |
| 4,838,886 A | 6/1989 | Kent |
| 4,842,666 A | 6/1989 | Werenicz |
| 4,846,815 A | 7/1989 | Scripps |
| 4,846,825 A | 7/1989 | Enloe et al. |
| 4,861,652 A | 8/1989 | Lippert et al. |
| 4,869,724 A | 9/1989 | Scripps |
| 4,886,697 A | 12/1989 | Perdelwitz, Jr et al. |
| 4,888,231 A | 12/1989 | Angstadt |
| 4,892,528 A | 1/1990 | Suzuki et al. |
| 4,892,535 A | 1/1990 | Bjornberg |
| 4,892,536 A | 1/1990 | DesMarais et al. |
| 4,894,060 A | 1/1990 | Nestegard |
| 4,894,277 A | 1/1990 | Akasaki |
| 4,900,317 A | 2/1990 | Buell |
| 4,904,251 A | 2/1990 | Igaue et al. |
| 4,909,802 A | 3/1990 | Ahr et al. |
| 4,909,803 A | 3/1990 | Aziz et al. |
| 4,936,839 A | 6/1990 | Molee |
| 4,940,463 A | 7/1990 | Leathers et al. |
| 4,940,464 A | 7/1990 | Van Gompel et al. |
| 4,946,527 A | 8/1990 | Battrell |
| 4,950,264 A | 8/1990 | Osborn |
| 4,960,477 A | 10/1990 | Mesek |
| 4,963,140 A | 10/1990 | Robertson et al. |
| 4,968,313 A | 11/1990 | Sabee |
| 4,990,147 A | 2/1991 | Freeland |
| 4,994,053 A | 2/1991 | Lang |
| 5,006,394 A | 4/1991 | Baird |
| 5,019,063 A | 5/1991 | Marsan et al. |
| 5,019,072 A | 5/1991 | Polski |
| 5,021,051 A | 6/1991 | Hiuke |
| 5,030,314 A * | 7/1991 | Lang ............... A61F 13/15634 156/390 |
| 5,032,120 A | 7/1991 | Freeland et al. |
| 5,034,008 A | 7/1991 | Breitkopf |
| 5,037,416 A | 8/1991 | Allen et al. |
| 5,051,536 A | 9/1991 | Gorton et al. |
| 5,071,414 A | 12/1991 | Elliott |
| 5,072,687 A * | 12/1991 | Mitchell ............... A61F 13/536 118/308 |
| 5,085,654 A | 2/1992 | Buell |
| 5,087,255 A | 2/1992 | Sims et al. |
| 5,092,861 A | 3/1992 | Nomura et al. |
| 5,102,597 A | 4/1992 | Roe et al. |
| 5,114,420 A | 5/1992 | Igaue et al. |
| 5,124,188 A | 6/1992 | Roe et al. |
| 5,135,522 A | 8/1992 | Fahrenkrug et al. |
| 5,137,537 A | 8/1992 | Herron et al. |
| D329,697 S | 9/1992 | Fahrenkrug et al. |
| 5,143,679 A | 9/1992 | Weber et al. |
| 5,147,343 A | 9/1992 | Kellenberger |
| 5,147,345 A | 9/1992 | Young et al. |
| 5,149,334 A | 9/1992 | Roe et al. |
| 5,149,335 A | 9/1992 | Kellenberger et al. |
| 5,151,091 A | 9/1992 | Glaug |
| 5,151,092 A | 9/1992 | Buell et al. |
| 5,156,793 A | 10/1992 | Buell et al. |
| 5,167,653 A | 12/1992 | Igaue et al. |
| 5,167,897 A | 12/1992 | Weber et al. |
| 5,175,046 A | 12/1992 | Nguyen |
| 5,180,622 A | 1/1993 | Berg et al. |
| 5,190,563 A | 3/1993 | Herron et al. |
| 5,190,606 A | 3/1993 | Merkatoris et al. |
| 5,204,997 A | 4/1993 | Suzuki et al. |
| 5,221,274 A | 6/1993 | Buell et al. |
| 5,235,515 A | 8/1993 | Ungpiyakul et al. |
| 5,242,436 A | 9/1993 | Weil et al. |
| 5,246,431 A | 9/1993 | Minetola et al. |
| 5,246,432 A | 9/1993 | Suzuki et al. |
| 5,246,433 A | 9/1993 | Hasse et al. |
| 5,248,309 A | 9/1993 | Serbiak et al. |
| 5,260,345 A | 11/1993 | Desmarais et al. |
| 5,269,775 A | 12/1993 | Freeland et al. |
| 5,281,683 A | 1/1994 | Yano et al. |
| H1298 H | 4/1994 | Ahr |
| 5,300,565 A | 4/1994 | Berg et al. |
| 5,312,386 A | 5/1994 | Correa et al. |
| 5,331,059 A | 7/1994 | Engelhardt et al. |
| 5,336,552 A | 8/1994 | Strack et al. |
| 5,348,547 A | 9/1994 | Payne et al. |
| 5,358,500 A | 10/1994 | LaVon et al. |
| 5,366,782 A | 11/1994 | Curro et al. |
| 5,387,207 A | 2/1995 | Dyer et al. |
| 5,387,209 A | 2/1995 | Yamamoto et al. |
| 5,389,095 A | 2/1995 | Suzuki |
| 5,397,316 A | 3/1995 | Lavon et al. |
| 5,399,175 A | 3/1995 | Glaug |
| 5,401,792 A | 3/1995 | Babu et al. |
| 5,409,771 A | 4/1995 | Dahmen et al. |
| H1440 H | 5/1995 | New et al. |
| 5,411,497 A | 5/1995 | Tanzer et al. |
| 5,415,644 A | 5/1995 | Enloe |
| 5,425,725 A | 6/1995 | Tanzer et al. |
| 5,433,715 A | 7/1995 | Tanzer et al. |
| 5,451,219 A | 9/1995 | Suzuki |
| 5,451,442 A | 9/1995 | Pieniak |
| 5,460,622 A | 10/1995 | Dragoo et al. |
| 5,462,541 A | 10/1995 | Bruemmer et al. |
| 5,476,458 A | 12/1995 | Glaug et al. |
| 5,486,166 A | 1/1996 | Bishop et al. |
| 5,490,846 A | 2/1996 | Ellis et al. |
| 5,492,962 A | 2/1996 | Lahrman et al. |
| 5,494,622 A * | 2/1996 | Heath ............... A61F 13/5323 156/276 |
| 5,499,978 A | 3/1996 | Buell et al. |
| 5,507,736 A | 4/1996 | Clear et al. |
| 5,507,895 A | 4/1996 | Suekane |
| 5,509,915 A | 4/1996 | Hanson et al. |
| 5,514,104 A | 5/1996 | Cole |
| 5,518,801 A | 5/1996 | Chappell et al. |
| 5,520,674 A | 5/1996 | Hines et al. |
| 5,522,810 A | 6/1996 | Allen, Jr. |
| 5,527,300 A | 6/1996 | Sauer |
| 5,531,730 A | 7/1996 | Dreier |
| 5,532,323 A | 7/1996 | Yano et al. |
| 5,542,943 A | 8/1996 | Sageser |
| 5,549,592 A | 8/1996 | Fries et al. |
| 5,549,593 A | 8/1996 | Ygge et al. |
| 5,549,791 A | 8/1996 | Herron et al. |

(56) References Cited

U.S. PATENT DOCUMENTS

| | | |
|---|---|---|
| 5,554,145 A | 9/1996 | Roe et al. |
| 5,560,878 A | 10/1996 | Dragoo et al. |
| 5,562,646 A | 10/1996 | Goldman et al. |
| 5,569,234 A | 10/1996 | Buell et al. |
| 5,571,096 A | 11/1996 | Dobrin et al. |
| 5,574,121 A | 11/1996 | Irie et al. |
| 5,580,411 A | 12/1996 | Nease et al. |
| 5,584,829 A | 12/1996 | Lavash et al. |
| 5,591,152 A | 1/1997 | Buell et al. |
| 5,591,155 A | 1/1997 | Nishikawa et al. |
| 5,593,399 A | 1/1997 | Tanzer et al. |
| 5,599,335 A | 2/1997 | Goldman et al. |
| 5,601,542 A | 2/1997 | Melius et al. |
| 5,607,414 A | 3/1997 | Richards et al. |
| 5,607,416 A | 3/1997 | Yamamoto et al. |
| 5,607,537 A | 3/1997 | Johnson et al. |
| 5,607,760 A | 3/1997 | Roe et al. |
| 5,609,587 A | 3/1997 | Roe |
| 5,609,588 A | 3/1997 | DiPalma et al. |
| 5,611,879 A | 3/1997 | Morman |
| 5,613,959 A | 3/1997 | Roessler et al. |
| 5,613,960 A | 3/1997 | Mizutani |
| 5,614,283 A | 3/1997 | Potnis et al. |
| 5,622,589 A | 4/1997 | Johnson et al. |
| 5,624,423 A | 4/1997 | Anjur |
| 5,624,424 A | 4/1997 | Saisaka et al. |
| 5,626,571 A | 5/1997 | Young et al. |
| 5,628,741 A | 5/1997 | Buell et al. |
| 5,635,191 A | 6/1997 | Roe et al. |
| 5,635,271 A | 6/1997 | Zafiroglu |
| 5,637,106 A | 6/1997 | Mitchell et al. |
| 5,643,238 A | 7/1997 | Baker |
| 5,643,243 A | 7/1997 | Klemp |
| 5,643,588 A | 7/1997 | Roe et al. |
| 5,649,914 A | 7/1997 | Glaug |
| 5,650,214 A | 7/1997 | Anderson et al. |
| H1674 H | 8/1997 | Ames et al. |
| 5,658,268 A | 8/1997 | Johns et al. |
| 5,662,634 A | 9/1997 | Yamamoto et al. |
| 5,662,638 A | 9/1997 | Johnson et al. |
| 5,674,215 A | 10/1997 | Ronnberg |
| 5,683,374 A | 11/1997 | Yamamoto |
| 5,685,874 A | 11/1997 | Buell et al. |
| 5,690,627 A | 11/1997 | Clear et al. |
| 5,691,035 A | 11/1997 | Chappell et al. |
| 5,691,036 A | 11/1997 | Lin et al. |
| 5,695,488 A | 12/1997 | Sosalla |
| 5,700,254 A | 12/1997 | McDowall et al. |
| 5,702,376 A | 12/1997 | Glaug |
| 5,714,156 A | 2/1998 | Schmidt et al. |
| 5,723,087 A | 3/1998 | Chappell et al. |
| 5,733,275 A | 3/1998 | Davis et al. |
| 5,749,866 A | 5/1998 | Roe et al. |
| 5,752,947 A | 5/1998 | Awolin |
| 5,756,039 A | 5/1998 | Mcfall et al. |
| H1732 H | 6/1998 | Johnson |
| 5,762,641 A | 6/1998 | Bewick-Sonntag et al. |
| 5,766,388 A * | 6/1998 | Pelley ............... A61F 13/15617 156/204 |
| 5,766,389 A | 6/1998 | Brandon et al. |
| 5,772,825 A | 6/1998 | Schmitz |
| 5,776,121 A | 7/1998 | Roe et al. |
| 5,779,831 A | 7/1998 | Schmitz |
| 5,788,684 A | 8/1998 | Abuto et al. |
| 5,795,345 A | 8/1998 | Mizutani |
| 5,797,892 A | 8/1998 | Glaug |
| 5,797,894 A | 8/1998 | Cadieux et al. |
| 5,807,365 A | 9/1998 | Luceri |
| 5,810,796 A | 9/1998 | Kimura et al. |
| 5,810,800 A | 9/1998 | Hunter et al. |
| 5,814,035 A | 9/1998 | Gryskiewicz et al. |
| 5,820,618 A | 10/1998 | Roberts et al. |
| 5,827,257 A | 10/1998 | Fujioka |
| 5,830,202 A | 11/1998 | Bogdanski et al. |
| 5,833,678 A | 11/1998 | Ashton et al. |
| 5,837,789 A | 11/1998 | Stockhausen et al. |
| 5,843,059 A | 12/1998 | Niemeyer et al. |
| 5,846,231 A | 12/1998 | Fujioka et al. |
| 5,846,232 A | 12/1998 | Serbiak et al. |
| 5,849,816 A | 12/1998 | Suskind et al. |
| 5,851,204 A | 12/1998 | Mizutani |
| 5,855,572 A | 1/1999 | Schmidt |
| 5,858,013 A | 1/1999 | Kling |
| 5,865,823 A | 2/1999 | Curro |
| 5,865,824 A | 2/1999 | Chen |
| 5,873,868 A | 2/1999 | Nakahata |
| 5,876,391 A | 3/1999 | Roe et al. |
| 5,891,118 A | 4/1999 | Toyoshima |
| 5,891,544 A | 4/1999 | Chappell et al. |
| 5,897,545 A | 4/1999 | Kline et al. |
| 5,904,673 A | 5/1999 | Roe et al. |
| 5,928,184 A | 7/1999 | Etheredge |
| 5,931,825 A | 8/1999 | Kuen et al. |
| 5,938,648 A | 8/1999 | Lavon et al. |
| 5,938,650 A | 8/1999 | Baer et al. |
| 5,941,862 A | 8/1999 | Haynes et al. |
| 5,944,706 A | 8/1999 | Palumbo et al. |
| 5,947,949 A | 9/1999 | Inoue et al. |
| 5,957,908 A | 9/1999 | Kline et al. |
| 5,968,025 A | 10/1999 | Roe et al. |
| 5,968,029 A | 10/1999 | Chappell et al. |
| 5,980,500 A | 11/1999 | Shimizu et al. |
| 5,981,824 A | 11/1999 | Luceri |
| 5,989,236 A | 11/1999 | Roe et al. |
| 6,004,306 A | 12/1999 | Robles et al. |
| 6,022,430 A | 2/2000 | Blenke et al. |
| 6,022,431 A | 2/2000 | Blenke et al. |
| 6,042,673 A | 3/2000 | Johnson et al. |
| 6,050,984 A | 4/2000 | Fujioka et al. |
| 6,054,631 A | 4/2000 | Gent |
| 6,060,115 A | 5/2000 | Borowski et al. |
| 6,068,620 A | 5/2000 | Chmielewski |
| 6,080,909 A | 6/2000 | Osterdahl et al. |
| 6,083,210 A | 7/2000 | Young et al. |
| 6,090,994 A | 7/2000 | Chen |
| 6,091,336 A | 7/2000 | Zand |
| 6,099,515 A | 8/2000 | Sugito |
| 6,102,892 A | 8/2000 | Putzer et al. |
| 6,103,814 A | 8/2000 | Van Drongelen et al. |
| 6,107,537 A | 8/2000 | Elder et al. |
| 6,110,157 A | 8/2000 | Schmidt |
| 6,117,121 A | 9/2000 | Faulks et al. |
| 6,117,803 A | 9/2000 | Morman et al. |
| 6,120,486 A | 9/2000 | Toyoda et al. |
| 6,120,487 A | 9/2000 | Ashton |
| 6,120,489 A | 9/2000 | Johnson et al. |
| 6,120,866 A | 9/2000 | Arakawa et al. |
| 6,121,509 A | 9/2000 | Ashraf et al. |
| 6,129,717 A | 10/2000 | Fujioka et al. |
| 6,129,720 A | 10/2000 | Blenke et al. |
| 6,132,411 A | 10/2000 | Huber et al. |
| 6,139,912 A | 10/2000 | Onuschak |
| 6,143,821 A | 11/2000 | Houben |
| 6,152,908 A | 11/2000 | Widlund |
| 6,156,023 A | 12/2000 | Yoshioka |
| 6,156,424 A | 12/2000 | Taylor |
| 6,160,197 A | 12/2000 | Lassen |
| 6,165,160 A | 12/2000 | Suzuki et al. |
| 6,174,302 B1 | 1/2001 | Kumasaka |
| 6,177,606 B1 | 1/2001 | Etheredge |
| 6,177,607 B1 | 1/2001 | Blaney et al. |
| 6,186,996 B1 | 2/2001 | Martin |
| 6,210,386 B1 | 4/2001 | Inoue |
| 6,210,390 B1 | 4/2001 | Karlsson |
| 6,231,556 B1 | 5/2001 | Osborn, III |
| 6,231,566 B1 | 5/2001 | Lai |
| 6,238,380 B1 | 5/2001 | Sasaki |
| 6,241,716 B1 | 6/2001 | Rönnberg |
| 6,258,996 B1 | 7/2001 | Goldman |
| 6,265,488 B1 | 7/2001 | Fujino et al. |
| 6,306,122 B1 | 10/2001 | Narawa et al. |
| 6,315,765 B1 | 11/2001 | Datta |
| 6,322,552 B1 | 11/2001 | Blenke et al. |
| 6,325,787 B1 | 12/2001 | Roe et al. |

(56) References Cited

U.S. PATENT DOCUMENTS

| | | | |
|---|---|---|---|
| 6,326,525 B1 | 12/2001 | Hamajima et al. |
| 6,334,858 B1 | 1/2002 | Ronnberg et al. |
| 6,336,922 B1 | 1/2002 | VanGompel et al. |
| 6,340,611 B1 | 1/2002 | Shimizu |
| 6,342,715 B1 | 1/2002 | Shimizu |
| 6,350,332 B1 | 2/2002 | Thomas et al. |
| 6,368,687 B1 | 4/2002 | Joseph et al. |
| 6,371,948 B1 | 4/2002 | Mizutani |
| 6,372,952 B1 | 4/2002 | Lash et al. |
| 6,375,644 B2 | 4/2002 | Mizutani |
| 6,376,034 B1 | 4/2002 | Brander |
| 6,383,431 B1 | 5/2002 | Dobrin et al. |
| 6,383,960 B1 | 5/2002 | Everett et al. |
| 6,394,989 B2 | 5/2002 | Mizutani |
| 6,402,729 B1 | 6/2002 | Boberg et al. |
| 6,402,731 B1 | 6/2002 | Suprise et al. |
| 6,403,857 B1 | 6/2002 | Gross et al. |
| 6,409,883 B1 | 6/2002 | Makolin |
| 6,410,820 B1 | 6/2002 | McFall et al. |
| 6,410,822 B1 | 6/2002 | Mizutani |
| 6,413,248 B1 | 7/2002 | Mizutani |
| 6,413,249 B1 | 7/2002 | Turi et al. |
| 6,414,214 B1 | 7/2002 | Engelhardt et al. |
| 6,419,667 B1 | 7/2002 | Avalon et al. |
| 6,423,046 B1 | 7/2002 | Fujioka et al. |
| 6,423,048 B1 | 7/2002 | Suzuki et al. |
| 6,423,884 B1 | 7/2002 | Oehmen |
| 6,429,350 B1 | 8/2002 | Tanzer et al. |
| 6,432,094 B1 | 8/2002 | Fujioka et al. |
| 6,432,098 B1 | 8/2002 | Kline et al. |
| 6,432,099 B2 | 8/2002 | Ronnberg |
| 6,437,214 B1 | 8/2002 | Everett et al. |
| 6,441,268 B1 | 8/2002 | Edwardsson |
| 6,443,933 B1 | 9/2002 | Suzuki et al. |
| 6,444,064 B1 | 9/2002 | Henry et al. |
| 6,447,496 B1 | 9/2002 | Mizutani |
| 6,458,111 B1 | 10/2002 | Onishi et al. |
| 6,458,877 B1 | 10/2002 | Ahmed et al. |
| 6,459,016 B1 | 10/2002 | Rosenfeld et al. |
| 6,461,342 B2 | 10/2002 | Tanji et al. |
| 6,461,343 B1 | 10/2002 | Schaefer et al. |
| 6,472,478 B1 | 10/2002 | Funk et al. |
| 6,475,201 B2 | 11/2002 | Saito et al. |
| 6,494,872 B1 | 12/2002 | Suzuki et al. |
| 6,494,873 B2 | 12/2002 | Karlsson et al. |
| 6,500,159 B1 | 12/2002 | Carvalho |
| 6,503,233 B1 | 1/2003 | Chen et al. |
| 6,503,979 B1 | 1/2003 | Funk et al. |
| 6,506,186 B1 | 1/2003 | Roessler |
| 6,506,961 B1 | 1/2003 | Levy |
| 6,515,195 B1 | 2/2003 | Lariviere |
| 6,517,525 B1 | 2/2003 | Berthou |
| 6,518,479 B1 | 2/2003 | Graef |
| 6,520,947 B1 | 2/2003 | Tilly et al. |
| 6,521,811 B1 | 2/2003 | Lassen |
| 6,521,812 B1 | 2/2003 | Howard et al. |
| 6,524,294 B1 | 2/2003 | Hilston et al. |
| 6,525,240 B1 | 2/2003 | Graef |
| 6,528,698 B2 | 3/2003 | Mizutani et al. |
| 6,531,025 B1 | 3/2003 | Lender et al. |
| 6,531,027 B1 | 3/2003 | Lender et al. |
| 6,534,149 B1 | 3/2003 | Daley et al. |
| 6,559,081 B1 | 5/2003 | Erspamer |
| 6,559,239 B1 | 5/2003 | Riegel et al. |
| 6,562,168 B1 | 5/2003 | Schmitt et al. |
| 6,562,192 B1 | 5/2003 | Hamilton |
| 6,569,137 B2 | 5/2003 | Suzuki et al. |
| 6,573,422 B1 | 6/2003 | Rosenfeld |
| 6,585,713 B1 | 7/2003 | LeMahieu et al. |
| 6,585,858 B1 | 7/2003 | Otto et al. |
| 6,602,234 B2 | 8/2003 | Klemp et al. |
| 6,605,070 B2 | 8/2003 | Ludwig et al. |
| 6,605,172 B1 | 8/2003 | Anderson et al. |
| 6,605,752 B2 | 8/2003 | Magnusson et al. |
| 6,610,900 B1 | 8/2003 | Tanzer |
| 6,630,054 B1 | 10/2003 | Graef |
| 6,632,209 B1 | 10/2003 | Chmielewski |
| 6,632,504 B1 | 10/2003 | Gillespie et al. |
| 6,645,569 B2 | 11/2003 | Cramer et al. |
| 6,646,180 B1 | 11/2003 | Chmielewski |
| 6,648,869 B1 | 11/2003 | Gillies et al. |
| 6,648,870 B1 | 11/2003 | Itoh et al. |
| 6,648,871 B2 | 11/2003 | Kusibojoska et al. |
| 6,649,807 B2 | 11/2003 | Mizutani |
| 6,649,810 B1 | 11/2003 | Minato et al. |
| 6,657,015 B1 | 12/2003 | Riegel et al. |
| 6,657,102 B2 | 12/2003 | Furuya |
| 6,667,424 B1 | 12/2003 | Hamilton |
| 6,670,522 B1 | 12/2003 | Graef |
| 6,673,982 B1 | 1/2004 | Chen |
| 6,673,983 B1 | 1/2004 | Graef |
| 6,673,985 B2 | 1/2004 | Mizutani |
| 6,682,515 B1 | 1/2004 | Mizutani et al. |
| 6,682,516 B2 | 1/2004 | Johnston |
| 6,689,115 B1 | 2/2004 | Popp et al. |
| 6,689,934 B2 | 2/2004 | Dodge, II et al. |
| 6,695,827 B2 | 2/2004 | Chen |
| 6,700,034 B1 | 3/2004 | Lindsay et al. |
| 6,703,538 B2 | 3/2004 | Lassen |
| 6,705,465 B2 | 3/2004 | Ling et al. |
| 6,706,943 B2 | 3/2004 | Onishi |
| 6,710,224 B2 | 3/2004 | Chmielewski et al. |
| 6,710,225 B1 | 3/2004 | Everett et al. |
| 6,716,205 B2 | 4/2004 | Popp et al. |
| 6,716,441 B1 | 4/2004 | Roe et al. |
| 6,717,029 B2 | 4/2004 | Baker |
| 6,726,668 B2 | 4/2004 | Underhill et al. |
| 6,726,792 B1 | 4/2004 | Johnson et al. |
| 6,734,335 B1 | 5/2004 | Graef |
| 6,790,798 B1 | 9/2004 | Suzuki et al. |
| 6,809,158 B2 | 10/2004 | Ikeuchi et al. |
| 6,818,083 B2 | 11/2004 | McAmish et al. |
| 6,830,800 B2 | 12/2004 | Curro et al. |
| 6,840,929 B2 | 1/2005 | Kurata |
| 6,846,374 B2 | 1/2005 | Popp |
| 6,858,771 B2 | 2/2005 | Yoshimasa |
| 6,863,933 B2 | 3/2005 | Cramer et al. |
| 6,863,960 B2 | 3/2005 | Curro et al. |
| 6,867,345 B2 | 3/2005 | Shimoe et al. |
| 6,867,346 B1 | 3/2005 | Dopps |
| 6,878,433 B2 | 4/2005 | Curro et al. |
| 6,880,211 B2 | 4/2005 | Jackson et al. |
| 6,891,080 B2 | 5/2005 | Minato |
| 6,904,865 B2 | 6/2005 | Klofta |
| 6,911,574 B1 | 6/2005 | Mizutani |
| 6,923,797 B2 | 8/2005 | Shinohara et al. |
| 6,926,703 B2 | 8/2005 | Sugito et al. |
| 6,929,629 B2 | 8/2005 | Drevik |
| 6,939,914 B2 | 9/2005 | Qin et al. |
| 6,946,585 B2 | 9/2005 | Brown |
| 6,953,451 B2 | 10/2005 | Berba |
| 6,955,733 B2 | 10/2005 | Henry et al. |
| 6,962,578 B1 | 11/2005 | Lavon |
| 6,962,645 B2 | 11/2005 | Graef et al. |
| 6,965,058 B1 | 11/2005 | Raidel |
| 6,969,781 B2 | 11/2005 | Graef |
| 6,972,010 B2 | 12/2005 | Pesce |
| 6,972,011 B2 | 12/2005 | Maeda et al. |
| 7,001,167 B2 * | 2/2006 | Venturino ......... A61F 13/15626 264/121 |
| 7,014,632 B2 | 3/2006 | Takino et al. |
| 7,015,370 B2 | 3/2006 | Watanabe |
| 7,037,299 B2 | 5/2006 | Turi et al. |
| 7,037,571 B2 | 5/2006 | Fish et al. |
| 7,048,726 B2 | 5/2006 | Kusagawa et al. |
| 7,056,311 B2 | 6/2006 | Kinoshita |
| 7,067,711 B2 | 6/2006 | Kinoshita et al. |
| 7,073,373 B2 | 7/2006 | La Fortune |
| 7,078,583 B2 | 7/2006 | Kudo e |
| 7,090,665 B2 | 8/2006 | Ohashi |
| 7,108,759 B2 | 9/2006 | You |
| 7,108,916 B2 | 9/2006 | Ehrnsperger et al. |
| 7,112,621 B2 | 9/2006 | Rohrbaugh et al. |
| 7,122,713 B2 | 10/2006 | Komatsu et al. |

(56) References Cited

U.S. PATENT DOCUMENTS

| | | |
|---|---|---|
| 7,125,470 B2 | 10/2006 | Graef |
| 7,132,585 B2 | 11/2006 | Kudo et al. |
| 7,147,628 B2 | 12/2006 | Drevik |
| 7,150,729 B2 | 12/2006 | Shimada et al. |
| 7,154,019 B2 | 12/2006 | Mishima et al. |
| 7,160,281 B2 | 1/2007 | Leminh et al. |
| 7,166,190 B2 | 1/2007 | Graef |
| 7,169,136 B2 | 1/2007 | Otsubo |
| 7,183,360 B2 | 2/2007 | Daniel et al. |
| 7,189,888 B2 | 3/2007 | Wang et al. |
| 7,196,241 B2 | 3/2007 | Kinoshita |
| 7,199,211 B2 | 4/2007 | Popp et al. |
| 7,204,830 B2 | 4/2007 | Mishima |
| 7,207,978 B2 | 4/2007 | Takino |
| 7,219,403 B2 | 5/2007 | Miyamoto et al. |
| 7,220,251 B2 | 5/2007 | Otsubo et al. |
| 7,250,481 B2 | 7/2007 | Jaworek et al. |
| 7,252,657 B2 | 8/2007 | Mishima |
| 7,265,258 B2 | 9/2007 | Hamilton |
| RE39,919 E | 11/2007 | Dodge, II et al. |
| 7,311,968 B2 | 12/2007 | Ehrnsperger et al. |
| 7,312,372 B2 | 12/2007 | Miyama |
| 7,318,820 B2 | 1/2008 | LaVon et al. |
| 7,329,244 B2 | 2/2008 | Otsubo |
| 7,329,246 B2 | 2/2008 | Kinoshita |
| 7,335,810 B2 | 2/2008 | Yoshimasa et al. |
| 7,377,914 B2 | 5/2008 | LaVon |
| 7,429,689 B2 | 9/2008 | Chen |
| 7,435,244 B2 | 10/2008 | Schroer et al. |
| 7,465,373 B2 | 12/2008 | Graef |
| 7,500,969 B2 | 3/2009 | Mishima |
| 7,504,552 B2 | 3/2009 | Tamura |
| 7,521,109 B2 | 4/2009 | Suzuki et al. |
| 7,521,587 B2 | 4/2009 | Busam et al. |
| 7,537,832 B2 | 5/2009 | Carlucci et al. |
| 7,547,815 B2 | 6/2009 | Ohashi |
| 7,550,646 B2 | 6/2009 | Tamura |
| 7,563,257 B2 | 7/2009 | Nakajima |
| 7,588,561 B2 | 9/2009 | Kenmochi |
| 7,594,904 B2 | 9/2009 | Rosenfeld |
| 7,625,363 B2 | 12/2009 | Yoshimasa |
| 7,641,642 B2 | 1/2010 | Murai et al. |
| 7,648,490 B2 | 1/2010 | Kuroda |
| 7,652,111 B2 | 1/2010 | Hermeling et al. |
| 7,666,173 B2 | 2/2010 | Mishima |
| 7,666,174 B2 | 2/2010 | Kawakami et al. |
| 7,686,790 B2 | 3/2010 | Rasmussen et al. |
| 7,687,596 B2 | 3/2010 | Hermeling et al. |
| 7,695,461 B2 | 4/2010 | Rosenfeld |
| 7,696,402 B2 | 4/2010 | Nishikawa |
| 7,708,725 B2 | 5/2010 | Tamagawa |
| 7,717,150 B2 | 5/2010 | Manabe |
| 7,722,587 B2 | 5/2010 | Suzuki et al. |
| 7,722,590 B2 | 5/2010 | Tsuji |
| 7,727,217 B2 | 6/2010 | Hancock-Cooke |
| 7,736,351 B2 | 6/2010 | Nigam |
| 7,744,576 B2 | 6/2010 | Busam et al. |
| 7,744,578 B2 | 6/2010 | Tanio et al. |
| 7,750,203 B2 | 7/2010 | Becker et al. |
| 7,754,822 B2 | 7/2010 | Daniel et al. |
| 7,754,940 B2 | 7/2010 | Brisebois |
| 7,759,540 B2 | 7/2010 | Litvay et al. |
| 7,763,004 B2 | 7/2010 | Beck |
| 7,767,875 B2 | 8/2010 | Olson |
| 7,767,878 B2 | 8/2010 | Suzuki |
| 7,772,420 B2 | 8/2010 | Hermeling et al. |
| 7,786,341 B2 | 8/2010 | Schneider et al. |
| 7,795,492 B2 | 9/2010 | Vartiainen |
| 7,803,145 B2 | 9/2010 | Rosenfeld |
| 7,825,291 B2 | 11/2010 | Elfsberg et al. |
| 7,850,672 B2 | 12/2010 | Guidotti et al. |
| 7,851,667 B2 | 12/2010 | Becker et al. |
| 7,855,314 B2 | 12/2010 | Hanao |
| 7,857,797 B2 | 12/2010 | Kudo |
| 7,858,842 B2 | 12/2010 | Komatsu |
| 7,884,259 B2 | 2/2011 | Hanao |
| 7,888,549 B2 | 2/2011 | Jansson et al. |
| 7,910,797 B2 | 3/2011 | Nandrea |
| 7,935,207 B2 | 5/2011 | Zhao |
| 7,935,861 B2 | 5/2011 | Suzuki |
| 7,938,813 B2 | 5/2011 | Wang et al. |
| 7,942,858 B2 | 5/2011 | Francoeur |
| 7,951,126 B2 | 5/2011 | Nanjyo |
| 7,982,091 B2 | 7/2011 | Konawa |
| 7,993,319 B2 | 8/2011 | Sperl |
| 8,007,639 B2 * | 8/2011 | Gelli .................. B31F 1/07 156/349 |
| 8,017,827 B2 | 9/2011 | Hundorf et al. |
| 8,029,486 B2 | 10/2011 | Nakajima |
| 8,034,991 B2 | 10/2011 | Bruzadin et al. |
| 8,039,684 B2 | 10/2011 | Guidotti et al. |
| 8,052,454 B2 | 11/2011 | Polnyi |
| 8,057,620 B2 | 11/2011 | Perego et al. |
| 8,109,915 B2 | 2/2012 | Shimoe |
| 8,133,212 B2 | 3/2012 | Takada |
| 8,148,598 B2 | 4/2012 | Tsang et al. |
| 8,163,124 B2 | 4/2012 | Moriura et al. |
| 8,173,858 B2 | 5/2012 | Kuroda |
| 8,178,747 B2 | 5/2012 | Venturino et al. |
| 8,183,430 B2 | 5/2012 | Hakansson et al. |
| 8,186,296 B2 | 5/2012 | Brown et al. |
| 8,187,240 B2 | 5/2012 | Busam et al. |
| 8,198,506 B2 | 6/2012 | Venturino et al. |
| 8,211,815 B2 | 7/2012 | Baker |
| 8,236,715 B2 | 8/2012 | Schmidt et al. |
| 8,237,012 B2 | 8/2012 | Miyama |
| 8,246,594 B2 | 8/2012 | Sper |
| 8,258,367 B2 | 9/2012 | Lawson et al. |
| 8,268,424 B1 | 9/2012 | Suzuki |
| 8,273,943 B2 | 9/2012 | Noda |
| 8,283,516 B2 | 10/2012 | Litvay |
| 8,317,766 B2 | 11/2012 | Naoto |
| 8,317,768 B2 | 11/2012 | Larsson |
| 8,319,005 B2 | 11/2012 | Becker et al. |
| 8,343,123 B2 | 1/2013 | Noda |
| 8,343,296 B2 | 1/2013 | Blessing et al. |
| 8,361,047 B2 | 1/2013 | Mukai |
| 8,377,025 B2 | 2/2013 | Nakajima |
| 8,450,555 B2 | 5/2013 | Nhan et al. |
| 8,496,637 B2 | 7/2013 | Hundorf et al. |
| 8,519,213 B2 | 8/2013 | Venturino et al. |
| 8,524,355 B2 | 9/2013 | Nakaoka |
| 8,552,252 B2 | 10/2013 | Hundorf et al. |
| 8,568,566 B2 * | 10/2013 | Jackels ............. A61F 13/15658 118/239 |
| 8,581,019 B2 | 11/2013 | Carlucci et al. |
| 8,603,058 B2 | 12/2013 | Sperl et al. |
| 8,604,270 B2 | 12/2013 | Venturino et al. |
| 8,633,347 B2 | 1/2014 | Bianco et al. |
| 8,674,170 B2 | 3/2014 | Busam et al. |
| 8,766,031 B2 | 7/2014 | Becker et al. |
| 8,772,570 B2 | 7/2014 | Kawakami et al. |
| 8,785,715 B2 | 7/2014 | Wright et al. |
| 8,791,318 B2 | 7/2014 | Becker et al. |
| 2001/0007065 A1 | 7/2001 | Blanchard |
| 2001/0008964 A1 | 7/2001 | Kurata et al. |
| 2001/0016548 A1 | 8/2001 | Kugler et al. |
| 2001/0020157 A1 | 9/2001 | Mizutani |
| 2001/0037101 A1 | 11/2001 | Allan et al. |
| 2001/0044610 A1 | 11/2001 | Kim |
| 2002/0007167 A1 | 1/2002 | Dan |
| 2002/0007169 A1 | 1/2002 | Graef et al. |
| 2002/0016122 A1 | 2/2002 | Curro et al. |
| 2002/0016579 A1 | 2/2002 | Stenberg |
| 2002/0045881 A1 | 4/2002 | Kusibojoska et al. |
| 2002/0056516 A1 * | 5/2002 | Ochi ..................... B26D 7/10 156/269 |
| 2002/0062112 A1 | 5/2002 | Mizutani |
| 2002/0062116 A1 | 5/2002 | Mizutani et al. |
| 2002/0065498 A1 | 5/2002 | Ohashi |
| 2002/0072471 A1 | 6/2002 | Ikeuchi et al. |
| 2002/0082575 A1 | 6/2002 | Dan |
| 2002/0087139 A1 | 7/2002 | Popp et al. |
| 2002/0102392 A1 | 8/2002 | Fish et al. |

(56) References Cited

U.S. PATENT DOCUMENTS

| | | |
|---|---|---|
| 2002/0115969 A1 | 8/2002 | Maeda et al. |
| 2002/0123728 A1 | 9/2002 | Graef et al. |
| 2002/0151634 A1 | 10/2002 | Rohrbaugh et al. |
| 2002/0151861 A1 | 10/2002 | Klemp et al. |
| 2002/0173767 A1 | 11/2002 | Popp et al. |
| 2002/0192366 A1 | 12/2002 | Cramer et al. |
| 2003/0036741 A1 | 2/2003 | Abba et al. |
| 2003/0078553 A1 | 4/2003 | Wada |
| 2003/0084983 A1 | 5/2003 | Rangachari et al. |
| 2003/0088223 A1 | 5/2003 | Vogt et al. |
| 2003/0105190 A1 | 6/2003 | Diehl et al. |
| 2003/0114816 A1 | 6/2003 | Underhill |
| 2003/0114818 A1 | 6/2003 | Benecke et al. |
| 2003/0120235 A1 | 6/2003 | Boulanger |
| 2003/0135181 A1 | 7/2003 | Chen et al. |
| 2003/0135182 A1 | 7/2003 | Woon et al. |
| 2003/0139712 A1 | 7/2003 | Dodge |
| 2003/0139715 A1 | 7/2003 | Dodge |
| 2003/0139718 A1 | 7/2003 | Graef |
| 2003/0144642 A1 | 7/2003 | Dopps |
| 2003/0144644 A1 | 7/2003 | Murai et al. |
| 2003/0148684 A1 | 8/2003 | Cramer et al. |
| 2003/0148694 A1 | 8/2003 | Ghiam |
| 2003/0167045 A1 | 9/2003 | Graef |
| 2003/0171727 A1 | 9/2003 | Graef |
| 2003/0208175 A1 | 11/2003 | Gross |
| 2003/0225385 A1 | 12/2003 | Glaug |
| 2003/0233082 A1 | 12/2003 | Kline et al. |
| 2003/0236512 A1 | 12/2003 | Baker |
| 2004/0019338 A1 | 1/2004 | Litvay et al. |
| 2004/0022998 A1 | 2/2004 | Miyamoto et al. |
| 2004/0033750 A1 | 2/2004 | Everett |
| 2004/0063367 A1 | 4/2004 | Dodge |
| 2004/0064115 A1 | 4/2004 | Arora |
| 2004/0064116 A1 | 4/2004 | Arora |
| 2004/0064125 A1 | 4/2004 | Justmann et al. |
| 2004/0065420 A1 | 4/2004 | Graef et al. |
| 2004/0082928 A1 | 4/2004 | Pesce et al. |
| 2004/0097895 A1 | 5/2004 | Busam et al. |
| 2004/0122411 A1 | 6/2004 | Hancock-Cooke |
| 2004/0127871 A1 | 7/2004 | Odorzynski |
| 2004/0127872 A1 | 7/2004 | Petryk |
| 2004/0134596 A1 | 7/2004 | Rosati et al. |
| 2004/0138633 A1 | 7/2004 | Mishima et al. |
| 2004/0147890 A1 | 7/2004 | Nakahata et al. |
| 2004/0158212 A1 | 8/2004 | Ponomarenko et al. |
| 2004/0162536 A1 | 8/2004 | Becker et al. |
| 2004/0167486 A1 | 8/2004 | Busam et al. |
| 2004/0167489 A1 | 8/2004 | Kellenberger et al. |
| 2004/0193127 A1 | 9/2004 | Hansson |
| 2004/0215160 A1 | 10/2004 | Chmielewski |
| 2004/0220541 A1 | 11/2004 | Suzuki et al. |
| 2004/0225271 A1 | 11/2004 | Datta et al. |
| 2004/0231065 A1 | 11/2004 | Daniel et al. |
| 2004/0236299 A1 | 11/2004 | Tsang et al. |
| 2004/0249355 A1 | 12/2004 | Tanio et al. |
| 2004/0260259 A1 | 12/2004 | Baker |
| 2005/0004543 A1 | 1/2005 | Schroer et al. |
| 2005/0004548 A1 | 1/2005 | Otsubo et al. |
| 2005/0008839 A1 | 1/2005 | Cramer et al. |
| 2005/0038401 A1 | 2/2005 | Suzuki et al. |
| 2005/0070867 A1 | 3/2005 | Beruda et al. |
| 2005/0085784 A1 | 4/2005 | LeMinh et al. |
| 2005/0090789 A1 | 4/2005 | Graef |
| 2005/0137543 A1 | 6/2005 | Underhill et al. |
| 2005/0148258 A1 | 7/2005 | Chakravarty |
| 2005/0148990 A1 | 7/2005 | Shimoe |
| 2005/0154363 A1 | 7/2005 | Minato |
| 2005/0159720 A1 | 7/2005 | Gentilcore |
| 2005/0165208 A1 | 7/2005 | Popp et al. |
| 2005/0171499 A1 | 8/2005 | Nigam et al. |
| 2005/0176910 A1 | 8/2005 | Jaworek et al. |
| 2005/0203475 A1 | 9/2005 | LaVon et al. |
| 2005/0215752 A1 | 9/2005 | Popp et al. |
| 2005/0229543 A1 | 10/2005 | Tippey |
| 2005/0245684 A1 | 11/2005 | Daniel et al. |
| 2005/0288645 A1 | 12/2005 | LaVon |
| 2005/0288646 A1 | 12/2005 | LaVon |
| 2006/0004334 A1 | 1/2006 | Schlinz et al. |
| 2006/0021695 A1 | 2/2006 | Blessing et al. |
| 2006/0024433 A1* | 2/2006 | Blessing ............ A61F 13/15764 427/180 |
| 2006/0069371 A1 | 3/2006 | Ohashi et al. |
| 2006/0073969 A1 | 4/2006 | Torli et al. |
| 2006/0081348 A1 | 4/2006 | Graef |
| 2006/0129114 A1 | 6/2006 | Mason et al. |
| 2006/0142724 A1 | 6/2006 | Watanabe |
| 2006/0155057 A1 | 7/2006 | Hermeling et al. |
| 2006/0155254 A1 | 7/2006 | Sanz et al. |
| 2006/0167215 A1 | 7/2006 | Hermeling et al. |
| 2006/0177647 A1 | 8/2006 | Schmidt et al. |
| 2006/0178071 A1 | 8/2006 | Schmidt et al. |
| 2006/0184146 A1 | 8/2006 | Suzuki |
| 2006/0184149 A1 | 8/2006 | Kasai et al. |
| 2006/0189954 A1 | 8/2006 | Kudo |
| 2006/0201643 A1* | 9/2006 | Underhill ............... B31F 1/07 162/117 |
| 2006/0202380 A1 | 9/2006 | Bentley |
| 2006/0206091 A1 | 9/2006 | Cole |
| 2006/0211828 A1 | 9/2006 | Daniel |
| 2006/0240229 A1 | 10/2006 | Ehrnsperger et al. |
| 2006/0264860 A1 | 11/2006 | Beck |
| 2006/0264861 A1 | 11/2006 | Lavon et al. |
| 2007/0027436 A1 | 2/2007 | Nakagawa et al. |
| 2007/0032770 A1 | 2/2007 | LaVon et al. |
| 2007/0043191 A1 | 2/2007 | Hermeling et al. |
| 2007/0043330 A1 | 2/2007 | Lankhof et al. |
| 2007/0073253 A1 | 3/2007 | Miyama |
| 2007/0078422 A1 | 4/2007 | Glaug et al. |
| 2007/0088308 A1 | 4/2007 | Ehrnsperger et al. |
| 2007/0093164 A1 | 4/2007 | Nakaoka |
| 2007/0093767 A1 | 4/2007 | Carlucci et al. |
| 2007/0100307 A1 | 5/2007 | Nomoto |
| 2007/0118087 A1 | 5/2007 | Flohr et al. |
| 2007/0123834 A1 | 5/2007 | McDowall et al. |
| 2007/0156108 A1 | 7/2007 | Becker et al. |
| 2007/0156110 A1 | 7/2007 | Thyfault |
| 2007/0167928 A1 | 7/2007 | Becker et al. |
| 2007/0179464 A1 | 8/2007 | Becker et al. |
| 2007/0179469 A1 | 8/2007 | Takahashi et al. |
| 2007/0191798 A1 | 8/2007 | Glaug |
| 2007/0219521 A1 | 9/2007 | Hird et al. |
| 2007/0219523 A1 | 9/2007 | Bruun |
| 2007/0244455 A1 | 10/2007 | Hansson et al. |
| 2007/0246147 A1* | 10/2007 | Venturino ......... A61F 13/15626 156/73.1 |
| 2007/0282288 A1 | 12/2007 | Noda |
| 2007/0282290 A1 | 12/2007 | Cole |
| 2007/0282291 A1 | 12/2007 | Cole |
| 2008/0027402 A1 | 1/2008 | Schmidt et al. |
| 2008/0032035 A1 | 2/2008 | Schmidt et al. |
| 2008/0091159 A1 | 4/2008 | Carlucci et al. |
| 2008/0119810 A1 | 5/2008 | Kuroda |
| 2008/0125735 A1 | 5/2008 | Busam et al. |
| 2008/0221538 A1 | 9/2008 | Zhao |
| 2008/0221539 A1 | 9/2008 | Zhao |
| 2008/0228158 A1 | 9/2008 | Sue et al. |
| 2008/0262459 A1 | 10/2008 | Kamoto |
| 2008/0268194 A1 | 10/2008 | Kim et al. |
| 2008/0274227 A1 | 11/2008 | Boatman et al. |
| 2008/0281287 A1 | 11/2008 | Marcelo |
| 2008/0294140 A1 | 11/2008 | Ecker et al. |
| 2008/0312617 A1 | 12/2008 | Hundorf et al. |
| 2008/0312618 A1* | 12/2008 | Hundorf ............. A61F 13/5323 604/366 |
| 2008/0312619 A1 | 12/2008 | Hundorf et al. |
| 2008/0312620 A1 | 12/2008 | Ashton et al. |
| 2008/0312621 A1 | 12/2008 | Hundorf et al. |
| 2008/0312622 A1 | 12/2008 | Hundorf et al. |
| 2008/0312623 A1 | 12/2008 | Hundorf et al. |
| 2008/0312624 A1 | 12/2008 | Hundorf et al. |
| 2008/0312625 A1 | 12/2008 | Hundorf et al. |
| 2008/0312627 A1 | 12/2008 | Takeuchi |
| 2008/0312628 A1 | 12/2008 | Hundorf et al. |

(56) References Cited

U.S. PATENT DOCUMENTS

| | | |
|---|---|---|
| 2009/0023848 A1 | 1/2009 | Ahmed et al. |
| 2009/0056867 A1* | 3/2009 | Moriura .......... A61F 13/15658 156/276 |
| 2009/0062760 A1 | 3/2009 | Wright et al. |
| 2009/0112173 A1 | 4/2009 | Bissah |
| 2009/0112175 A1 | 4/2009 | Bissah et al. |
| 2009/0157022 A1 | 6/2009 | MacDonald |
| 2009/0192035 A1 | 7/2009 | Stueven et al. |
| 2009/0240220 A1 | 9/2009 | Macdonald |
| 2009/0247977 A1 | 10/2009 | Takeuchi |
| 2009/0258994 A1 | 10/2009 | Stueven et al. |
| 2009/0270825 A1 | 10/2009 | Wciorka et al. |
| 2009/0298963 A1 | 12/2009 | Matsumoto et al. |
| 2009/0299312 A1 | 12/2009 | Macdonald |
| 2009/0306618 A1 | 12/2009 | Kudo |
| 2009/0318884 A1 | 12/2009 | Meyer et al. |
| 2010/0051166 A1* | 3/2010 | Hundorf .......... A61F 13/15658 156/62.8 |
| 2010/0062165 A1 | 3/2010 | Suzuki |
| 2010/0062934 A1 | 3/2010 | Suzuki |
| 2010/0063470 A1 | 3/2010 | Suzuki |
| 2010/0068520 A1 | 3/2010 | Stueven et al. |
| 2010/0100065 A1 | 4/2010 | Bianco |
| 2010/0121296 A1 | 5/2010 | Noda |
| 2010/0137773 A1 | 6/2010 | Gross |
| 2010/0137823 A1 | 6/2010 | Corneliusson |
| 2010/0198179 A1 | 8/2010 | Noda |
| 2010/0228210 A1 | 9/2010 | Busam et al. |
| 2010/0241097 A1 | 9/2010 | Nigam et al. |
| 2010/0262099 A1 | 10/2010 | Klofta |
| 2010/0274208 A1 | 10/2010 | Gabrielii |
| 2010/0274210 A1 | 10/2010 | Noda |
| 2010/0312208 A1 | 12/2010 | Bond et al. |
| 2010/0324521 A1 | 12/2010 | Mukai |
| 2010/0324523 A1 | 12/2010 | Mukai |
| 2010/0331801 A1 | 12/2010 | Kawakami et al. |
| 2011/0041999 A1 | 2/2011 | Hundorf et al. |
| 2011/0060303 A1 | 3/2011 | Bissah |
| 2011/0066127 A1 | 3/2011 | Kuwano |
| 2011/0071486 A1 | 3/2011 | Harada |
| 2011/0092944 A1 | 4/2011 | Sagisaka |
| 2011/0112498 A1 | 5/2011 | Nhan et al. |
| 2011/0125120 A1 | 5/2011 | Nishitani |
| 2011/0130732 A1* | 6/2011 | Jackels .......... A61F 13/15658 604/365 |
| 2011/0130737 A1 | 6/2011 | Sagisaka |
| 2011/0137276 A1 | 6/2011 | Yoshikawa |
| 2011/0144602 A1 | 6/2011 | Long |
| 2011/0144604 A1 | 6/2011 | Noda |
| 2011/0144606 A1 | 6/2011 | Nandrea |
| 2011/0152813 A1 | 6/2011 | Ellingson |
| 2011/0166540 A1 | 7/2011 | Yang et al. |
| 2011/0172630 A1 | 7/2011 | Nomoto |
| 2011/0174430 A1 | 7/2011 | Zhao |
| 2011/0208147 A1 | 8/2011 | Kawakami et al. |
| 2011/0250413 A1 | 10/2011 | Lu et al. |
| 2011/0268932 A1 | 11/2011 | Catalan et al. |
| 2011/0274834 A1 | 11/2011 | Brown et al. |
| 2011/0288513 A1 | 11/2011 | Hundorf et al. |
| 2011/0288514 A1 | 11/2011 | Kuroda |
| 2011/0319846 A1 | 12/2011 | Rinnert |
| 2011/0319848 A1 | 12/2011 | McKiernan et al. |
| 2011/0319851 A1 | 12/2011 | Kudo |
| 2012/0004633 A1 | 1/2012 | R. Marcelo |
| 2012/0016326 A1 | 1/2012 | Brennan et al. |
| 2012/0022479 A1 | 1/2012 | Cotton |
| 2012/0035566 A1 | 2/2012 | Sagisaka |
| 2012/0035576 A1 | 2/2012 | Ichikawa |
| 2012/0064792 A1 | 3/2012 | Bauduin |
| 2012/0071848 A1 | 3/2012 | Zhang |
| 2012/0165771 A1 | 6/2012 | Ruman et al. |
| 2012/0165776 A1 | 6/2012 | McGregor et al. |
| 2012/0175056 A1 | 7/2012 | Tsang |
| 2012/0184934 A1 | 7/2012 | Venturino |
| 2012/0232514 A1 | 9/2012 | Baker |
| 2012/0238977 A1 | 9/2012 | Oku |
| 2012/0253306 A1 | 10/2012 | Otsubo |
| 2012/0256750 A1 | 10/2012 | Novak |
| 2012/0270715 A1 | 10/2012 | Motegi et al. |
| 2012/0271262 A1 | 10/2012 | Venturino |
| 2012/0312491 A1 | 12/2012 | Jackels et al. |
| 2012/0316523 A1 | 12/2012 | Hippe et al. |
| 2012/0316526 A1 | 12/2012 | Rosati et al. |
| 2012/0316527 A1 | 12/2012 | Rosati et al. |
| 2012/0316528 A1 | 12/2012 | Kreuzer et al. |
| 2012/0316529 A1 | 12/2012 | Kreuzer et al. |
| 2012/0323195 A1 | 12/2012 | Ehrnsperger et al. |
| 2012/0323201 A1 | 12/2012 | Bissah |
| 2012/0323202 A1 | 12/2012 | Bissah |
| 2013/0035656 A1 | 2/2013 | Moriya et al. |
| 2013/0041334 A1 | 2/2013 | Prioleau |
| 2013/0211354 A1 | 8/2013 | Tsuji et al. |
| 2013/0218115 A1 | 8/2013 | Katsuragawa et al. |
| 2013/0226119 A1 | 8/2013 | Katsuragawa et al. |
| 2013/0226120 A1 | 8/2013 | Van De Maele |
| 2014/0005622 A1 | 1/2014 | Wirtz et al. |
| 2014/0005623 A1 | 1/2014 | Wirtz et al. |
| 2014/0039437 A1 | 2/2014 | Van De Maele |
| 2014/0045683 A1 | 2/2014 | Loick et al. |
| 2014/0135726 A1 | 5/2014 | Busam et al. |
| 2014/0142531 A1 | 5/2014 | Sasayama et al. |
| 2014/0163500 A1 | 6/2014 | Roe et al. |
| 2014/0163501 A1 | 6/2014 | Ehrnsperger et al. |
| 2014/0163502 A1 | 6/2014 | Arizti et al. |
| 2014/0163503 A1 | 6/2014 | Arizti et al. |
| 2014/0163506 A1 | 6/2014 | Roe et al. |
| 2014/0163511 A1 | 6/2014 | Roe et al. |
| 2014/0324007 A1 | 10/2014 | Hundorf et al. |
| 2014/0324008 A1 | 10/2014 | Hundorf et al. |

FOREIGN PATENT DOCUMENTS

| | | |
|---|---|---|
| CA | 2308961 | 11/2000 |
| CA | 2487027 | 12/2003 |
| CA | 2561521 | 3/2007 |
| CA | 2630713 | 11/2008 |
| CA | 2636673 | 1/2009 |
| CA | 2712563 | 8/2010 |
| CA | 2702001 | 10/2010 |
| CN | 1238171 A | 12/1999 |
| CN | 2362468 Y | 2/2000 |
| CN | 2527254 Y | 12/2002 |
| CN | 2535020 Y | 2/2003 |
| CN | 2548609 Y | 5/2003 |
| CN | 1539391 | 10/2004 |
| CN | 1939242 | 4/2007 |
| CN | 101292930 | 10/2008 |
| CN | 201263750 | 7/2009 |
| CN | 201591689 | 9/2010 |
| CN | 201855366 U | 6/2011 |
| DE | 32059312 C2 | 9/1983 |
| DE | 3608114 A1 | 9/1987 |
| DE | 4 335 919 A | 4/1995 |
| DE | 19732499 | 2/1999 |
| DE | 10204937 A1 | 8/2003 |
| EP | 0083022 | 7/1983 |
| EP | 149880 | 7/1985 |
| EP | 0149880 A2 | 7/1985 |
| EP | 0203289 A2 | 12/1986 |
| EP | 0206208 | 12/1986 |
| EP | 209561 B1 | 1/1987 |
| EP | 0297411 B1 | 1/1989 |
| EP | 0304957 | 3/1989 |
| EP | 0374542 | 6/1990 |
| EP | 0394274 | 10/1990 |
| EP | 0403832 | 12/1990 |
| EP | 0481322 B1 | 4/1992 |
| EP | 0530438 | 3/1993 |
| EP | 0547847 | 6/1993 |
| EP | 0555346 | 8/1993 |
| EP | 0559476 | 9/1993 |
| EP | 0591647 B2 | 4/1994 |
| EP | 0597273 B1 | 5/1994 |
| EP | 0601610 B2 | 6/1994 |

(56) References Cited

FOREIGN PATENT DOCUMENTS

| | | |
|---|---|---|
| EP | 0632068 | 1/1995 |
| EP | 0640330 A1 | 3/1995 |
| EP | 0668066 | 9/1995 |
| EP | 0685214 | 12/1995 |
| EP | 0687453 | 12/1995 |
| EP | 0 691 133 A1 | 1/1996 |
| EP | 0689817 | 1/1996 |
| EP | 0724418 | 8/1996 |
| EP | 0725613 | 8/1996 |
| EP | 0725615 | 8/1996 |
| EP | 0725616 | 8/1996 |
| EP | 0758543 | 2/1997 |
| EP | 0761194 | 3/1997 |
| EP | 0769284 | 4/1997 |
| EP | 0781537 | 7/1997 |
| EP | 0783877 B1 | 7/1997 |
| EP | 0787472 | 8/1997 |
| EP | 0788874 B1 | 8/1997 |
| EP | 0796068 | 9/1997 |
| EP | 0799004 | 10/1997 |
| EP | 0875224 A1 | 1/1998 |
| EP | 0822794 B1 | 2/1998 |
| EP | 0826351 | 3/1998 |
| EP | 0844861 | 6/1998 |
| EP | 0863733 | 9/1998 |
| EP | 0971751 | 9/1998 |
| EP | 0880955 | 12/1998 |
| EP | 0891758 | 1/1999 |
| EP | 0893115 | 1/1999 |
| EP | 0904755 | 3/1999 |
| EP | 0916327 | 5/1999 |
| EP | 0925769 A2 | 6/1999 |
| EP | 0933074 | 8/1999 |
| EP | 0937736 | 8/1999 |
| EP | 0941157 | 9/1999 |
| EP | 0947549 | 10/1999 |
| EP | 0951887 B1 | 10/1999 |
| EP | 0951890 | 10/1999 |
| EP | 2295493 | 10/1999 |
| EP | 2305749 | 10/1999 |
| EP | 2330152 | 10/1999 |
| EP | 0953326 | 11/1999 |
| EP | 0978263 A1 | 2/2000 |
| EP | 0985397 B1 | 3/2000 |
| EP | 1005847 | 6/2000 |
| EP | 1008333 | 6/2000 |
| EP | 1013252 B1 | 6/2000 |
| EP | 1018999 | 7/2000 |
| EP | 1019002 B1 | 7/2000 |
| EP | 1019003 B1 | 7/2000 |
| EP | 1022008 | 7/2000 |
| EP | 1023884 | 8/2000 |
| EP | 1053729 | 11/2000 |
| EP | 1059072 A2 | 12/2000 |
| EP | 1063954 | 1/2001 |
| EP | 1071388 | 1/2001 |
| EP | 1078618 | 2/2001 |
| EP | 1088537 A2 | 4/2001 |
| EP | 1116479 A2 | 7/2001 |
| EP | 1132069 | 9/2001 |
| EP | 1173128 | 1/2002 |
| EP | 1175194 B1 | 1/2002 |
| EP | 1184018 | 3/2002 |
| EP | 1192312 B1 | 4/2002 |
| EP | 1196122 B2 | 4/2002 |
| EP | 1199059 | 4/2002 |
| EP | 1199327 | 4/2002 |
| EP | 1208824 | 5/2002 |
| EP | 0793469 | 6/2002 |
| EP | 1210925 | 6/2002 |
| EP | 1224922 | 7/2002 |
| EP | 1225857 | 7/2002 |
| EP | 1262531 A1 | 12/2002 |
| EP | 1263374 B1 | 12/2002 |
| EP | 1275358 | 1/2003 |
| EP | 1275361 | 1/2003 |
| EP | 1293187 | 3/2003 |
| EP | 1304986 B1 | 5/2003 |
| EP | 1332742 B1 | 8/2003 |
| EP | 1339368 | 9/2003 |
| EP | 1374817 | 1/2004 |
| EP | 1388334 | 2/2004 |
| EP | 1402863 | 3/2004 |
| EP | 0962208 | 8/2004 |
| EP | 1447066 | 8/2004 |
| EP | 1447067 | 8/2004 |
| EP | 1460987 | 9/2004 |
| EP | 0963749 | 11/2004 |
| EP | 1495739 | 1/2005 |
| EP | 1524955 | 4/2005 |
| EP | 1920743 | 4/2005 |
| EP | 1541103 | 6/2005 |
| EP | 1551344 | 7/2005 |
| EP | 1586289 | 10/2005 |
| EP | 1588723 | 10/2005 |
| EP | 1605882 | 12/2005 |
| EP | 1609448 | 12/2005 |
| EP | 1 621 166 A1 | 2/2006 |
| EP | 1621167 | 2/2006 |
| EP | 1632206 | 3/2006 |
| EP | 1642556 | 4/2006 |
| EP | 1656162 | 5/2006 |
| EP | 1669046 | 6/2006 |
| EP | 1688114 | 8/2006 |
| EP | 2314265 | 8/2006 |
| EP | 1723939 | 11/2006 |
| EP | 1738727 | 1/2007 |
| EP | 1754461 | 2/2007 |
| EP | 1787611 | 5/2007 |
| EP | 1813238 | 8/2007 |
| EP | 2008626 | 12/2008 |
| EP | 2055279 A1 | 5/2009 |
| EP | 2093049 | 8/2009 |
| EP | 2130522 | 12/2009 |
| EP | 2444046 | 4/2012 |
| EP | 2532328 | 12/2012 |
| EP | 2532329 A1 | 12/2012 |
| EP | 2532332 A1 | 12/2012 |
| EP | 2679210 A1 | 1/2014 |
| EP | 2740449 | 6/2014 |
| EP | 2740450 | 6/2014 |
| EP | 2740452 | 6/2014 |
| ES | 2213491 | 8/2004 |
| FR | 2566631 | 1/1986 |
| FR | 2612770 | 9/1988 |
| FR | 2 690 843 A | 11/1993 |
| FR | 2810234 | 12/2001 |
| GB | 1333081 A | 8/1971 |
| GB | 1307441 | 2/1973 |
| GB | 1513055 | 6/1978 |
| GB | 2101468 | 1/1983 |
| GB | 2170108 | 7/1986 |
| GB | 2262873 | 7/1993 |
| GB | 2288540 A | 6/1994 |
| GB | 2354449 | 3/2001 |
| GB | 2452260 A | 10/2007 |
| GR | 851769 | 11/1985 |
| IN | 0984/KOL/19999 | 10/2005 |
| IN | 212479 B | 3/2007 |
| IN | 208543 B | 8/2007 |
| IN | 0980/MUM/2009 | 6/2009 |
| JP | 55-72928 U | 5/1980 |
| JP | 59-8322 U | 1/1984 |
| JP | 63-0148323 U | 9/1988 |
| JP | 03-224481 B2 | 10/1991 |
| JP | 04-122256 | 4/1992 |
| JP | 06-269475 A | 7/1994 |
| JP | 10-328232 | 12/1998 |
| JP | 11-033056 A | 2/1999 |
| JP | 11-318980 | 11/1999 |
| JP | 2000-232985 | 8/2000 |
| JP | 2000-238161 | 9/2000 |
| JP | 04-392936 B2 | 10/2000 |
| JP | 2001-037810 | 2/2001 |

(56) References Cited

FOREIGN PATENT DOCUMENTS

| | | |
|---|---|---|
| JP | 2001-046435 A | 2/2001 |
| JP | 2001-120597 | 5/2001 |
| JP | 2001-158074 | 6/2001 |
| JP | 2001-178768 A | 7/2001 |
| JP | 2001-198157 | 7/2001 |
| JP | 2001-224626 A | 8/2001 |
| JP | 03-420481 B2 | 11/2001 |
| JP | 2001-353174 A | 12/2001 |
| JP | 2002-052042 A | 2/2002 |
| JP | 2002-11380 A | 4/2002 |
| JP | 2002-165832 | 6/2002 |
| JP | 2002-165836 | 6/2002 |
| JP | 2002-272769 A | 9/2002 |
| JP | 2002-325792 A | 11/2002 |
| JP | 2002-325799 A | 11/2002 |
| JP | 2002-369841 A | 12/2002 |
| JP | 2003/144487 A | 5/2003 |
| JP | 2003-153955 A | 5/2003 |
| JP | 2003-265524 A | 9/2003 |
| JP | 2003-275237 | 9/2003 |
| JP | 2004-089269 | 3/2004 |
| JP | 03-566012 B2 | 6/2004 |
| JP | 03-568146 B2 | 6/2004 |
| JP | 03-616077 B2 | 11/2004 |
| JP | 2004-337314 A | 12/2004 |
| JP | 2004-337385 A | 12/2004 |
| JP | 2004350864 | 12/2004 |
| JP | 03-640475 B2 | 1/2005 |
| JP | 2005-00312 A | 1/2005 |
| JP | 03-660816 B2 | 3/2005 |
| JP | 03-676219 B2 | 5/2005 |
| JP | 03-688403 B2 | 6/2005 |
| JP | 03 705943 B2 | 8/2005 |
| JP | 03-719819 B2 | 9/2005 |
| JP | 03-724963 B2 | 9/2005 |
| JP | 03-725008 B2 | 9/2005 |
| JP | 03-737376 B2 | 11/2005 |
| JP | 2006-014792 A | 1/2006 |
| JP | 03-781617 B2 | 3/2006 |
| JP | 2006-110329 | 4/2006 |
| JP | 03-801449 B2 | 5/2006 |
| JP | 2006-116036 A | 5/2006 |
| JP | 03-850102 B2 | 9/2006 |
| JP | 03-850207 B2 | 9/2006 |
| JP | 03-856941 B2 | 9/2006 |
| JP | 03-868628 B2 | 10/2006 |
| JP | 03-874499 B2 | 11/2006 |
| JP | 03-877702 B2 | 11/2006 |
| JP | 2006-325639 A | 12/2006 |
| JP | 2006-346021 | 12/2006 |
| JP | 03-904356 B2 | 1/2007 |
| JP | 2007-007455 A | 1/2007 |
| JP | 2007-007456 A | 1/2007 |
| JP | 03-926042 B2 | 3/2007 |
| JP | 03-934855 B2 | 3/2007 |
| JP | 2007/054219 A | 3/2007 |
| JP | 2007-089906 A | 4/2007 |
| JP | 2007-105198 A | 4/2007 |
| JP | 2007-152033 A | 6/2007 |
| JP | 03-986210 B2 | 7/2007 |
| JP | 03-986222 B2 | 7/2007 |
| JP | 2007-167453 | 7/2007 |
| JP | 2007-175515 A | 7/2007 |
| JP | 2007-195665 A | 8/2007 |
| JP | 2007-267763 A | 10/2007 |
| JP | 2007-275491 A | 10/2007 |
| JP | 04-035341 B2 | 11/2007 |
| JP | 04-058281 B2 | 12/2007 |
| JP | 04-061086 B2 | 12/2007 |
| JP | 04-092319 B2 | 3/2008 |
| JP | 2008-080150 A | 4/2008 |
| JP | 2008-0936289 A | 4/2008 |
| JP | 04-124322 B2 | 5/2008 |
| JP | 2008-119081 A | 5/2008 |
| JP | 2008-136739 A | 6/2008 |
| JP | 2008-136877 A | 6/2008 |
| JP | 04-148594 B2 | 7/2008 |
| JP | 04-148620 B2 | 7/2008 |
| JP | 2008-1549606 A | 7/2008 |
| JP | 04-162609 B2 | 8/2008 |
| JP | 04-162637 B2 | 8/2008 |
| JP | 04-166923 B2 | 8/2008 |
| JP | 04-167406 B2 | 8/2008 |
| JP | 04-173723 B2 | 8/2008 |
| JP | 04-190675 B2 | 9/2008 |
| JP | 04-190693 B2 | 9/2008 |
| JP | 04-208338 B2 | 10/2008 |
| JP | 2008-246089 | 10/2008 |
| JP | 04-230971 B2 | 12/2008 |
| JP | 2008-295475 A | 12/2008 |
| JP | 2008-295713 A | 12/2008 |
| JP | 04-261593 B2 | 2/2009 |
| JP | 2009-112590 | 5/2009 |
| JP | 04-322228 B2 | 6/2009 |
| JP | 2009-136601 | 6/2009 |
| JP | 2009-1472401 A | 7/2009 |
| JP | 2009-201878 A | 9/2009 |
| JP | 2009-232987 A | 10/2009 |
| JP | 2009-261777 A | 11/2009 |
| JP | 2009-291473 A | 12/2009 |
| JP | 2009-297048 A | 12/2009 |
| JP | 20100178342 | 1/2010 |
| JP | 04-458702 B2 | 2/2010 |
| JP | 04-459013 B2 | 2/2010 |
| JP | 2010-022560 | 2/2010 |
| JP | 04-481325 B2 | 3/2010 |
| JP | 2010-051654 A | 3/2010 |
| JP | 2010-063814 A | 3/2010 |
| JP | 2010-063944 A | 3/2010 |
| JP | 04-492957 B2 | 4/2010 |
| JP | 2010-068954 A | 4/2010 |
| JP | 2010-075462 A | 4/2010 |
| JP | 2010-082059 A | 4/2010 |
| JP | 2010-104545 A | 5/2010 |
| JP | 2010-104547 A | 5/2010 |
| JP | 2010-110535 A | 5/2010 |
| JP | 2010-119454 A | 6/2010 |
| JP | 2010-119605 A | 6/2010 |
| JP | 2010-119743 A | 6/2010 |
| JP | 2010-131131 A | 6/2010 |
| JP | 2010-131132 A | 6/2010 |
| JP | 2010-131206 | 6/2010 |
| JP | 2010-131297 A | 6/2010 |
| JP | 2010-136917 A | 6/2010 |
| JP | 2010-136937 A | 6/2010 |
| JP | 2010-194124 A | 6/2010 |
| JP | 04-540563 B2 | 7/2010 |
| JP | 04-587947 B2 | 9/2010 |
| JP | 2010-201093 | 9/2010 |
| JP | 2010-221067 | 10/2010 |
| JP | 04-67472 B2 | 11/2010 |
| JP | 04-620299 B2 | 11/2010 |
| JP | 04-627473 B2 | 11/2010 |
| JP | 04-638087 B2 | 12/2010 |
| JP | 04-695262 B | 12/2010 |
| JP | 2010-273842 A | 12/2010 |
| JP | 2010/284418 A | 12/2010 |
| JP | 2010-284418 A | 12/2010 |
| JP | 2011-000480 A | 1/2011 |
| JP | 2011-030700 | 2/2011 |
| JP | 04-693574 B2 | 3/2011 |
| JP | 2011-067484 A | 4/2011 |
| JP | 2011-072720 A | 4/2011 |
| JP | 2011-104014 | 6/2011 |
| JP | 2011-104122 A | 6/2011 |
| JP | 2011-120661 A | 6/2011 |
| JP | 2011-125360 A | 6/2011 |
| JP | 2011-125537 | 6/2011 |
| JP | 04-776516 B2 | 7/2011 |
| JP | 2011-130797 A | 7/2011 |
| JP | 2011-130799 A | 7/2011 |
| JP | 2011-156032 A | 8/2011 |
| JP | 2011-156070 A | 8/2011 |
| JP | 2011-156254 | 8/2011 |

(56) References Cited

FOREIGN PATENT DOCUMENTS

| | | |
|---|---|---|
| JP | 04-824882 B2 | 9/2011 |
| JP | 48-50272 B2 | 10/2011 |
| JP | 04-855533 B2 | 11/2011 |
| JP | 2011-239858 | 12/2011 |
| JP | 04-931572 B2 | 2/2012 |
| JP | 04-937225 B2 | 3/2012 |
| JP | 04-953618 B2 | 3/2012 |
| JP | 04-969437 B2 | 4/2012 |
| JP | 04-969640 B2 | 4/2012 |
| JP | 04-974524 B2 | 4/2012 |
| JP | 04-979780 B2 | 4/2012 |
| JP | 49-71491 B2 | 4/2012 |
| JP | 05-016020 B2 | 6/2012 |
| JP | 05-027364 B2 | 6/2012 |
| JP | 05-031082 B2 | 7/2012 |
| JP | 05-042351 B2 | 7/2012 |
| JP | 05-043569 B2 | 7/2012 |
| JP | 05-043591 B2 | 7/2012 |
| JP | 05-046488 B2 | 7/2012 |
| JP | 2012-125625 A | 7/2012 |
| JP | 05-053765 B2 | 8/2012 |
| JP | 05-070275 B2 | 8/2012 |
| JP | 05-079931 B1 | 9/2012 |
| JP | 05-080189 B2 | 9/2012 |
| JP | 05-084442 B2 | 9/2012 |
| JP | 05-084476 B2 | 9/2012 |
| JP | 05-089269 B2 | 9/2012 |
| JP | 50-85770 B2 | 9/2012 |
| JP | 05-113146 B2 | 10/2012 |
| JP | 05-129536 B2 | 11/2012 |
| JP | 05-105884 B2 | 12/2012 |
| KR | 20010005620 | 1/2001 |
| KR | 20020035634 | 5/2002 |
| KR | 20080028771 | 4/2008 |
| SE | 9400916 | 3/1994 |
| SE | 9704893 | 12/1997 |
| WO | WO90/15830 | 12/1990 |
| WO | WO93/21237 | 10/1993 |
| WO | WO93/21879 | 11/1993 |
| WO | WO95/10996 | 4/1995 |
| WO | WO95/11652 | 5/1995 |
| WO | WO95/14453 | 6/1995 |
| WO | WO95/15139 | 6/1995 |
| WO | WO95/16424 | 6/1995 |
| WO | WO95/16746 | 6/1995 |
| WO | WO95/19753 | 7/1995 |
| WO | WO95/21596 | 8/1995 |
| WO | WO95/24173 | 9/1995 |
| WO | WO95/29657 | 11/1995 |
| WO | WO95/32698 | 12/1995 |
| WO | WO95/34329 | 12/1995 |
| WO | WO96/16624 | 6/1996 |
| WO | WO96/19173 | 6/1996 |
| WO | WO97/11659 | 4/1997 |
| WO | WO97/17922 | 5/1997 |
| WO | WO98/16179 | 4/1998 |
| WO | WO98/16180 | 4/1998 |
| WO | WO98/43684 | 10/1998 |
| WO | WO99/13813 | 3/1999 |
| WO | WO99/34841 | 7/1999 |
| WO | WO99/51178 | 10/1999 |
| WO | WO00/00235 | 1/2000 |
| WO | WO00/32145 | 6/2000 |
| WO | WO00/59430 | 10/2000 |
| WO | WO01/15647 | 3/2001 |
| WO | WO01/26596 | 4/2001 |
| WO | WO02/07663 | 1/2002 |
| WO | WO02/32962 | 4/2002 |
| WO | WO02/064877 | 8/2002 |
| WO | WO02/067809 | 9/2002 |
| WO | WO03/009794 | 2/2003 |
| WO | WO03039402 | 5/2003 |
| WO | WO03/053297 | 7/2003 |
| WO | WO03/105738 | 12/2003 |
| WO | WO2004/021946 | 3/2004 |
| WO | WO2004/049995 | 6/2004 |
| WO | WO2004/071539 | 8/2004 |
| WO | WO2004/084784 | 10/2004 |
| WO | WO2004/105664 | 12/2004 |
| WO | WO2005/018694 | 3/2005 |
| WO | WO2005/087164 | 9/2005 |
| WO | WO2006/104024 | 5/2006 |
| WO | WO2006/059922 | 6/2006 |
| WO | WO2006/062258 | 6/2006 |
| WO | WO2006/066029 | 6/2006 |
| WO | WO2006/083584 | 8/2006 |
| WO | WO200/134904 | 12/2006 |
| WO | WO2006/134906 | 12/2006 |
| WO | WO2007/000315 | 1/2007 |
| WO | WO2007/046052 | 4/2007 |
| WO | WO2007/047598 | 4/2007 |
| WO | WO2007/049725 | 5/2007 |
| WO | WO2007/061035 | 5/2007 |
| WO | WO2007/142145 | 12/2007 |
| WO | WO2007/148502 | 12/2007 |
| WO | WO2008/018922 | 2/2008 |
| WO | WO2008/065945 | 6/2008 |
| WO | WO2008/146749 | 12/2008 |
| WO | WO2008/155699 | 12/2008 |
| WO | WO2009/004941 | 1/2009 |
| WO | WO2009/005431 | 1/2009 |
| WO | WO2009/139248 | 1/2009 |
| WO | WO2009/139255 | 1/2009 |
| WO | WO2009/041223 | 4/2009 |
| WO | WO2009/096108 | 8/2009 |
| WO | WO2009/107435 | 9/2009 |
| WO | WO2009/122830 | 10/2009 |
| WO | WO 2009/152018 A1 | 12/2009 |
| WO | WO2009/155264 | 12/2009 |
| WO | WO2009/155265 | 12/2009 |
| WO | WO2010/071508 | 6/2010 |
| WO | WO2010/074319 | 7/2010 |
| WO | WO2010/107096 | 9/2010 |
| WO | WO2010/114052 | 10/2010 |
| WO | WO2010/117015 | 10/2010 |
| WO | WO2011/053044 | 5/2011 |
| WO | WO2011/118725 | 9/2011 |
| WO | WO2011/118842 | 9/2011 |
| WO | WO2011/145653 | 11/2011 |
| WO | WO2011/150955 | 12/2011 |
| WO | WO2011/163582 | 12/2011 |
| WO | WO2012/002252 | 1/2012 |
| WO | WO2012/014436 | 2/2012 |
| WO | WO2012/042908 | 4/2012 |
| WO | WO2012/043077 | 4/2012 |
| WO | WO2012/043078 | 4/2012 |
| WO | WO2012/052172 | 4/2012 |
| WO | WO2012/043082 | 5/2012 |
| WO | WO2012/067216 | 5/2012 |
| WO | WO2012/073499 | 6/2012 |
| WO | WO2012074466 | 6/2012 |
| WO | WO2012/090508 | 7/2012 |
| WO | WO2012/091016 | 7/2012 |
| WO | WO2012/101934 | 8/2012 |
| WO | WO2012/102034 | 8/2012 |
| WO | WO2012/117824 | 9/2012 |
| WO | WO2012/132460 | 10/2012 |
| WO | WO2012/170778 | 12/2012 |
| WO | WO2012/170779 | 12/2012 |
| WO | WO2012/170781 | 12/2012 |
| WO | WO2012/170808 | 12/2012 |
| WO | WO2012/174026 | 12/2012 |
| WO | WO2013/001788 | 1/2013 |
| WO | WO2013/060733 | 5/2013 |
| WO | WO2014/078247 | 5/2014 |

OTHER PUBLICATIONS

International Search Report, PCT/US2012/041522, dated Sep. 5, 2012, 13 pages.

* cited by examiner

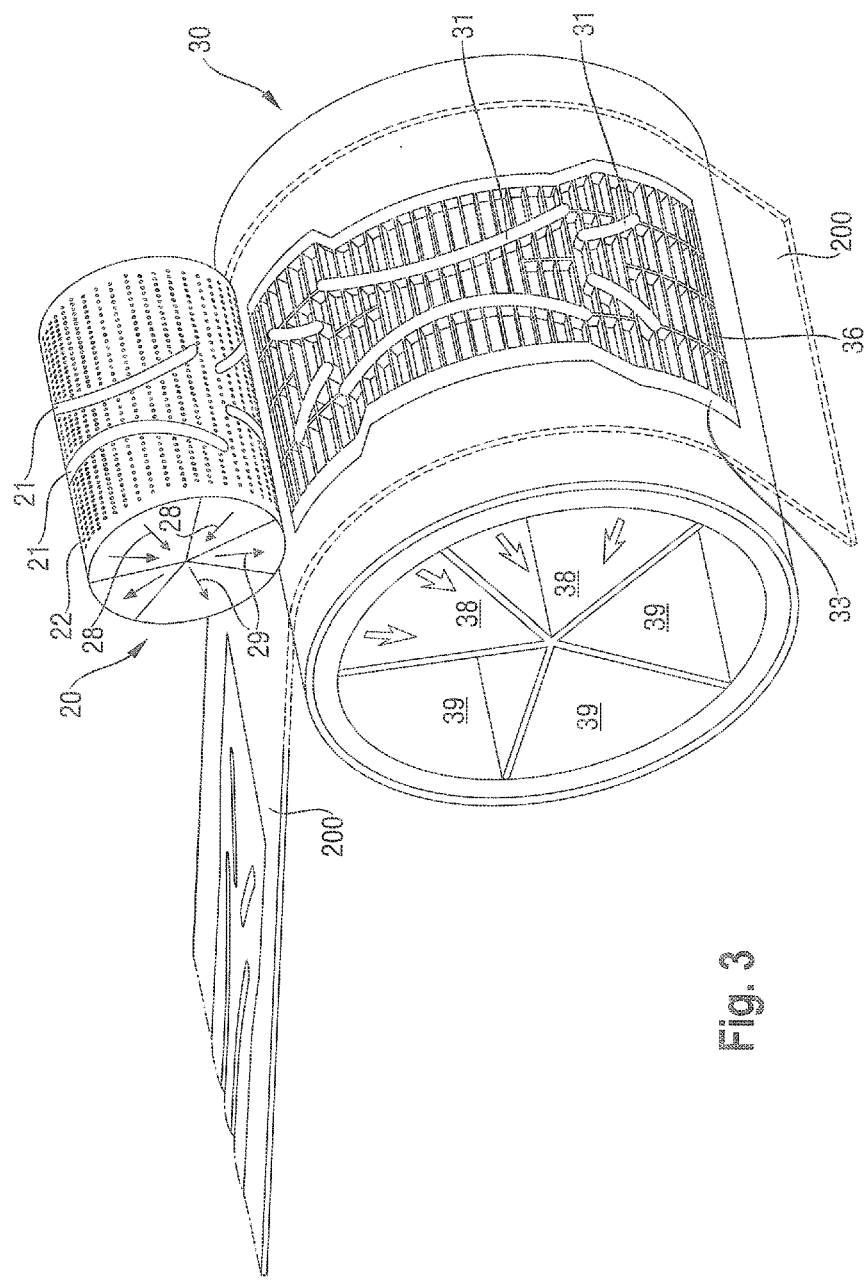

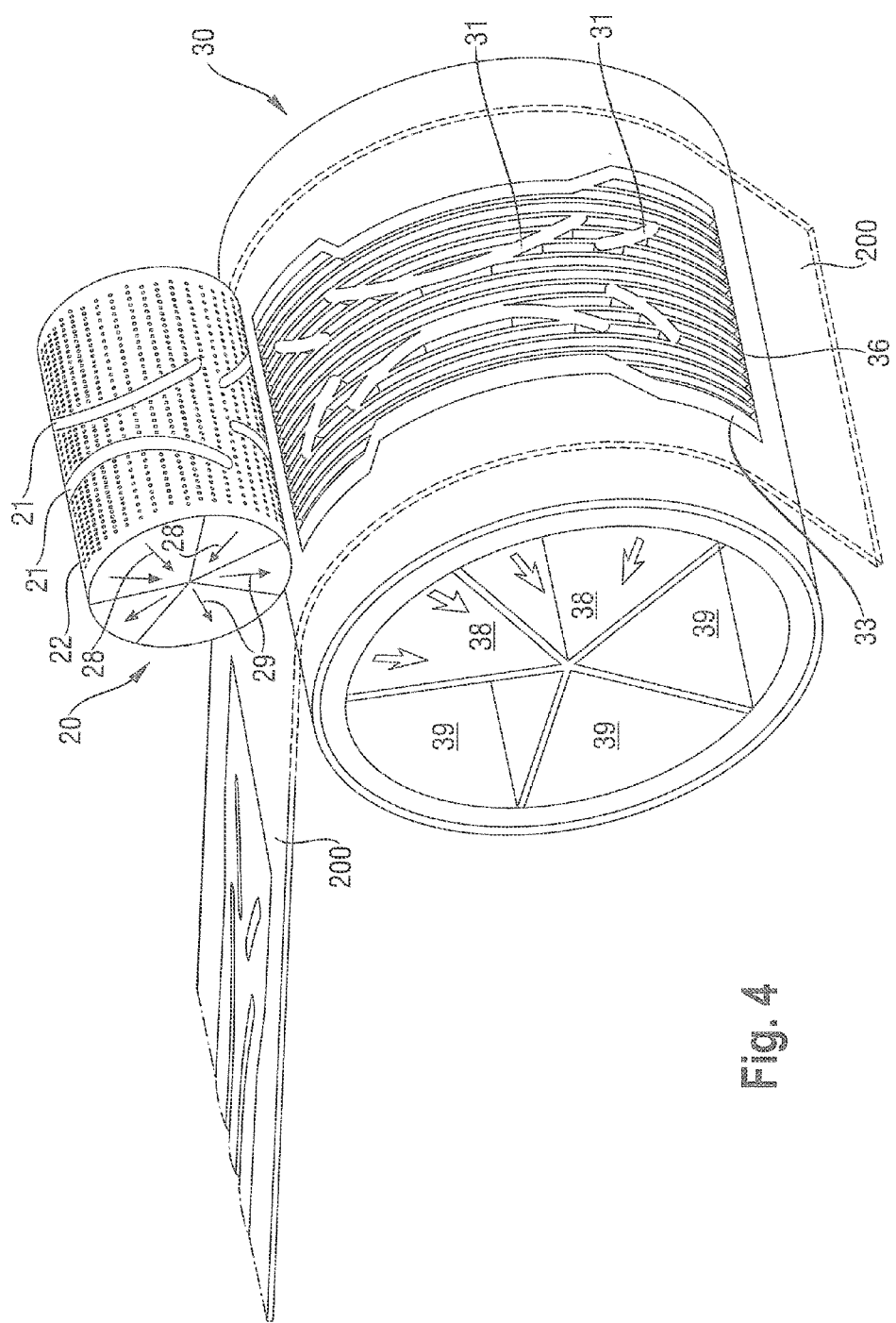

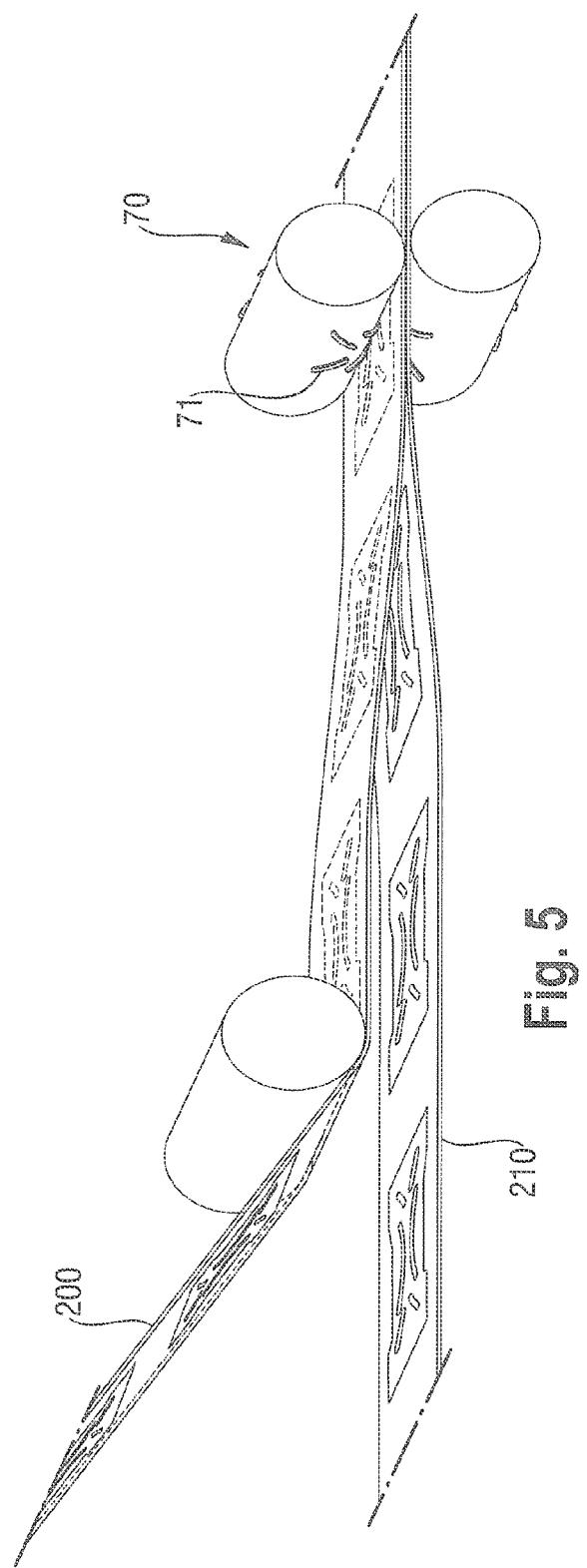

METHOD AND APPARATUS FOR MAKING ABSORBENT STRUCTURES WITH ABSORBENT MATERIAL

FIELD OF THE INVENTION

The present disclosure relates to a method for making an absorbent structure with strips that are free of absorbent material, by receiving absorbent material on a first surface with raised strips that do not receive absorbent material, and transferring it therewith to a second surface with mating strips, that meet with said raised strips, and that then do not receive absorbent material; and to apparatuses combining such first and second surfaces.

BACKGROUND OF THE INVENTION

Absorbent articles, such as diapers and sanitary napkins, absorb and contain body exudates. They also are intended to prevent body exudates from soiling, wetting, or otherwise contaminating clothing or other articles, such as bedding, that come in contact with the wearer. A disposable absorbent article, such as a disposable diaper, may be worn for several hours in a dry state or in a urine-loaded state. Accordingly, efforts have been made toward improving the fit and comfort of the absorbent article to the wearer, both when the article is dry and when the article is fully or partially loaded with liquid exudate, while maintaining or enhancing the absorbing and containing functions of the article.

Efforts have also been made to make absorbent article thinner when dry, to improve the comfort of such articles.

Some absorbent articles, like diapers, contain absorbent material such as super absorbent polymers that absorbs very high quantities of liquid and causes the absorbent article to swell significantly. Such articles will thus increase significantly in volume during use, and sometimes in particular in the crotch area between the wearer's legs, which may render the article uncomfortable.

There is thus still a need to further improve the fit of such articles and/or the liquid transportation away from the crotch. There is also a need to reduce the usage of absorbent material in such articles.

There is also still a need to further reduce the chance of leakage and to improve the efficiency of absorbency of an absorbent article, such as a diaper.

It has also been found that improved liquid transportation can be achieved by the provision of transportation channels for distributing liquid in the absorbent article, e.g. the absorbent structure thereof. Furthermore, it has surprisingly been found that the amount of absorbent material can be reduced hereby, whilst maintaining the performance. It has been found that improved fit can be obtained by providing absorbent articles with absorbent structures wherein the absorbent material is structured in machine direction, optionally with areas that comprise less or no absorbent material, for improved bending flexibility in use (in the direction corresponding to the machine direction).

The present disclosure provides an apparatus and method for providing such absorbent structures, having suitable transportation channels, which allow reduction of the usage of absorbent material and/or channels that improve fit/flexibility.

SUMMARY OF THE INVENTION

The present disclosure provides an apparatus (1) for making an absorbent structure comprising a supporting sheet (200) and thereon an absorbent layer with a longitudinal dimensional and transverse dimension and a height dimension, said absorbent layer comprising an absorbent material (100) with therein one or more channels that are substantially free of absorbent material, said apparatus (1) having:

a) a feeder (60) for feeding said absorbent material (100) to a first moving endless surface;

b) a transfer means for transferring a supporting sheet (200) to a second moving endless surface;

c) a first moving endless surface (20), having one or more absorbent layer-forming reservoirs (25) with a longitudinal dimension and averaged length, a perpendicular transverse dimension and average width, and, perpendicular to both, a depth dimension and average depth, and a void volume for receiving said absorbent material (100) therein, said reservoir(s) comprising one or more substantially longitudinally extending raised strips (21) (not having a void volume and hence not receiving said absorbent material (100) therein), each having an average width W of at least 5% of the average width of the reservoir (25) (in some embodiments optionally at least 5 mm), and an average length L of at least 5% and at the most 80% of the average longitudinal dimension of the reservoir; said reservoir(s) being for transferring said absorbent material (100) to said second moving endless surface (30) adjacent and in proximity thereto;

d) said second moving endless surface (30), having an outer shell that has one or more air permeable or partially air permeable receptacles (33) for receiving said supporting sheet (200) thereon or therein, and said receptacle (33) having one or more substantially longitudinally extending substantially mating strips (31), having each an average width W' of from 0.5×W to 1.2×W, optionally at least 2.5 mm, optionally having an average length L' being from about 0.8×L to 1.2×L provided at the most 90% of the longitudinal dimension of the reservoir, wherein said outer shell is optionally connected to one or more secondary vacuum systems for facilitating retention of said supporting sheet (200) and/or said absorbent material (100) thereon, and wherein, in a meeting point, said first moving endless surface (20) and said outer shell and/or second moving endless surface (30) are adjacent to one another and in close proximity of one another during transfer of said absorbent material (100) and wherein each mating strip (31) is adjacent and in close proximity to a raised strip (21) during transfer of said absorbent material.

The invention also provides methods using said apparatus (1) of the invention, and/or for making an absorbent structure with a longitudinal dimensional and transverse dimension and height dimension, and comprising a supporting sheet (200) and thereon an absorbent layer of absorbent material (100) and therein one or more channels with substantially no absorbent material, said method comprising the steps of:

a) providing a feeder (60) for feeding said absorbent material (100) to a first moving endless surface;

b) providing a transfer means for transferring a supporting sheet (200) to a second moving endless surface;

c) providing a first moving endless surface (20), having one or more absorbent layer-forming reservoirs (25) with a longitudinal dimension and averaged length, a perpendicular transverse dimension and average width, and, perpendicular to both, a depth dimension and average depth, and a void volume for receiving said absorbent material (100) therein, said reservoir(s) comprising one or more substantially longitudinally extending raised strips (21), each having an average width W of at least 5% of the average width of the reservoir, and an average length L of at least 5% and at the most 80% of the average longitudinal dimension of the reservoir; said reservoir(s) being for transferring said absorbent material (100) to said second moving endless surface (30) adjacent and in proximity thereto;

d) providing a second moving endless surface (30), having an outer shell that has one or more air permeable or partially air permeable receptacles (33) with for receiving said supporting sheet (200) thereon or therein, with a receiving area and with one or more substantially longitudinally extending mating strips (31) that may be air impermeable, and having each an average width W' of from 0.5×W to 1.2×W, an average length L' being from about 0.8×L to 1.2×L provided at the most 90% of the longitudinal dimension of the reservoir, wherein said outer shell is optionally connected to one or more secondary vacuum systems for facilitating retention of supporting sheet (200) and/or said absorbent material (100) thereon, and wherein, in a meeting point, said first moving endless surface (20) and said second surface (30)/outer shell are at least partially adjacent to one another and in close proximity of one another during transfer of said absorbent material (100) and such that each mating strip (31) is substantially completely adjacent and in close proximity to a raised strip (21) during transfer of said absorbent material;

e) feeding with said feeder (60) an absorbent material (100) to said first moving endless surface, in at least said reservoir(s) (25) thereof;

f) optionally, removing any absorbent material (100) on said raised strips (21);

g) simultaneously, transferring said supporting sheet (200) to said second moving endless surface, onto or into said receptacle (33);

h) selectively transferring in said meeting point, said absorbent material (100) with said first moving endless surface (20) only to said part of the supporting sheet (200) that is on or in said receiving area of said receptacle (33).

Said reservoir(s) (25) may be formed by of a multitude of grooves and/or cavities (22) with a void volume, for receiving said absorbent material (100) therein. In some embodiments, the average width W of (each) strip is optionally at least 6 mm, or for example at least 7 mm, and/or at least at least 7%, or for example at least 10% of the average width of the respective reservoir.

Said grooves and/or cavities (22) may each for example have a maximum dimension in transverse direction which is at least 3 mm, and wherein the shortest distance between directly neighboring cavities (22) and/or grooves in substantially transverse dimension, is less than 5 mm. Cavities (22) and/or grooves that are directly adjacent a raised strip (21) may have a volume that is more than the volume of one or more, or all of their neighboring cavities (22) or grooves, that are not directly adjacent said strip or another strip (thus further removed from a strip).

Said first moving endless surface's reservoir (25) may be at least partially air permeable and said first moving endless surface (20) may have a cylindrical surface with said reservoirs, rotatably moving around a stator, comprising a vacuum chamber (28) (and optionally a blow of chamber (29) to blow pressurized air through the reservoir onto said absorbent material just before the meeting point); said second moving surface's outershell may be cylindrical, rotatably moving around a stator, comprising a secondary vacuum chamber (38) connected to said secondary vacuum system (and optionally a blow of chamber (39) to blow pressurized air through the receptacle onto said absorbent structure to facilitate removal from the second moving endless surface).

Said receptacle(s) (33) may further comprise a multitude of substantially longitudinally extending rods (36), spaced apart from one another in transverse direction, for example, each rod having a maximum cross-machine dimension of at least 0.3 mm and the minimum distance in transverse dimension between neighboring rods (36) being at least 1 mm, and said rods (36) each having an average height dimension of at least 1 mm, optionally said rods (36) and said mating strips (31) being in the same plane of the outershell.

The apparatus (1) may comprise one or more adhesive application unit(s) (50;51) as described herein. Said adhesive application can be beneficial to immobilize said absorbent material, to ensure said channels remain substantially permanent in use and/or to help the supporting material adhere to a further material placed over said absorbent layer in said channels. The method may comprise the addition a step i):

i) 1) applying an adhesive material (i.e. a first adhesive material) to said absorbent structure produced in step g); and/or i) 2) applying an adhesive material (i.e. a second adhesive material) to said supporting sheet (200), prior or step f, or simultaneously therewith, but in any event prior to step h).

Step i) 1) may involve straying said first adhesive material in the form of fibers onto said absorbent layer, or part thereof, for example substantially continuously, so it is also present in said channels.

Step i) 2) may involve slot coating or spray-coating the supporting sheet (200), either continuously, or for example in a pattern corresponding to the channel pattern.

In some preferred embodiments herein, the apparatus (1) may have pressure roll (70) with a raised pressure pattern (71), substantially corresponding to the pattern of said mating strip(s)(31) and/or channels, for contacting selectively said absorbent structure's supporting sheet (200) and/or the further material, described herein after, in the areas corresponding to said channel (s) (only).

Said receptacle (33) of said second moving surface may have a first average width dimension and said supporting sheet (200), or said part thereof that is on said receptacle (33), has a second average width dimension, and the ratio of said first to said second average width dimension is at least 1:1.2.

By use of method and apparatus (1) herein, wherein the raised portions and mating strips (31) substantially mate during transfer of the absorbent material (100) to a supporting sheet (200) on said receptacle (33), e.g. on said mating strips (31), the absorbent structure may have said absorbent material (100) deposited on a layer with therein channels substantially without absorbent material; the absorbent layer may be in the form of strips of absorbent material (100) with therein, or therein between strips free of absorbent material (e.g. the crests of said supporting sheet (200)); in some embodiments herein, the supporting sheet (200) is formed into undulation(s) between neighboring matting strips, and/or between neighboring rods (36) that may be present, as described below, and the method and apparatus (1) herein is such that the absorbent material (100) is deposited in said undulations.

As described above, the supporting sheet (200) may be transferred to said second moving endless surface (30) such that it forms undulations and crests. Then, when the supporting sheet (200) is removed from said second moving endless surface, the supporting sheet (200) is pulled substantially flat, resulting in an absorbent structure with substantially longitudinally extending strips (that correspond to the crests of said material) that comprise substantially no absorbent material.

The invention also relates to absorbent structures, cores obtainable by the method herein or with the apparatus herein, and absorbent articles, such as pads or in particular diapers, comprising such a structure or core.

It should be understood that above and following description applies equally to the method and the apparatus (1) of the invention, and the absorbent structure obtained therewith, unless stated otherwise.

BRIEF DESCRIPTION OF THE DRAWINGS

FIG. 3 is a partial perspective view of an apparatus (1) of the present disclosure, or used in a method of the invention.

FIG. 4 is a partial perspective view of an alternative apparatus (1) of the present disclosure, or used in an alternative method of the invention.

FIG. 5 is a partial perspective view of an optional element of apparatus (1) of the present disclosure, or optionally used in a method of the invention.

DETAILED DESCRIPTION OF THE INVENTION

Figure 1A:
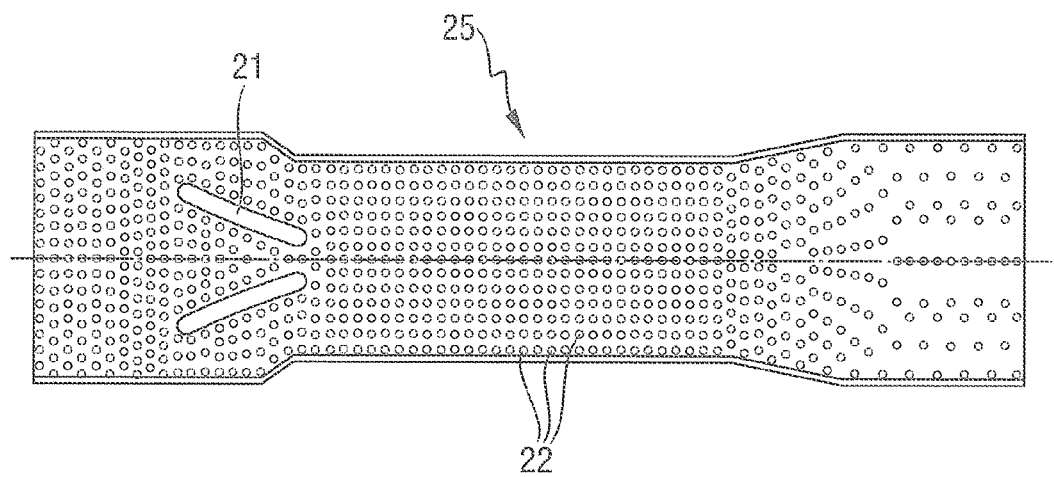
FIG. 1A is a top view of a reservoir (25) of the first moving endless surface (20) herein.

As summarized above, this invention encompasses a method and apparatus (1) for making an absorbent structure useful for absorbent article comprising absorbent material, optionally at least, or only, particulate superabsorbent polymer material, and preferred absorbent structure. Embodiments of such method and apparatus (1) and resulting absorbent structures and absorbent articles are further described herein after the following definitions.

Definitions

"Absorbent structure" refers to a three-dimension structure with a longitudinally dimension and perpendicular thereto a transverse dimension and perpendicular to both a height dimension, and that comprises at least an absorbent material (100) and a supporting sheet (200), and that is useful in an absorbent article.

"Absorbent layer" refers to a three dimensional layer of absorbent material, formed by deposition of absorbent material (100) onto the supporting sheet (200).

"Absorbent material" refers to a material or mixture of materials that can absorb and retain bodily fluids; it typically includes or consists of "superabsorbent polymer material".

"Superabsorbent polymer material" (also known as "absorbent gelling material," or "AGM," or "superabsorbent,") refer to polymeric material that can absorb at least 10 times 9 and typically at least 15 times or at least 20 times) their weight of an aqueous 0.9% saline solution as measured using the Centrifuge Retention Capacity test (Edana 441.2-02)., i.e. having a CRC of at least 10 g/g, and typically at least 15 g/g or at least 20 g/g.

"Particulate" is used herein to refer to a material which is in particulate form so as to be flowable in the dry state.

"Absorbent article" refers to a device that absorbs and contains body exudates, and, more specifically, refers to devices that are placed against or in proximity to the body of the wearer to absorb and contain the various exudates discharged from the body. Absorbent articles may include adult and infant diapers, including pants, such as infant training pants and adult incontinence undergarments, and feminine hygiene products, such as sanitary napkins and panty-liners and adult in continent pads, and breast pads, care mats, bibs, wound dressing products, and the like. Absorbent articles may further include floor cleaning articles, food industry articles, and the like. As used herein, the term "body fluids" or "body exudates" includes, but is not limited to, urine, blood, vaginal discharges, breast milk, sweat and fecal matter.

"Diaper" refers to an absorbent article generally worn by infants and incontinent persons about the lower torso so as to encircle the waist and legs of the wearer and that is specifically adapted to receive and contain urinary and fecal waste.

"Pant" or "training pant", as used herein, refer to diaper having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

A "nonwoven" is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Substantially cellulose free" is used herein to describe an article, such as an absorbent layer structure or core, that contains less than 5% by weight cellulosic fibers.

"Thickness" and "height" are used herein interchangeably.

A absorbent structure and absorbent layer thereof, and a receptacle (33) and a reservoir (25) herein each have a longitudinal dimension and average length, and this may be corresponding the machine direction (MD, and perpendicular thereto a transverse dimension, and average width, which may be corresponding to the cross-machine direction (CD); and a front region, back region and central region, each being ⅓ of the average length of the structure/layer, respectively, and having each the full width. Each has longitudinal edges and edge zones, extending the full length thereof- as further described below.

First Moving Endless Surface, e.g. Print Roll

The absorbent material (100) is delivered to the supporting sheet (200) by a first moving endless surface (20) placed adjacent and in close proximity to said second moving endless surface, for example substantially above said surface. The absorbent material (100) may be deposited substantially continuously. The point or area where the absorbent material (100) leaves the first moving endless surface (20) and transfers to said second moving endless surface (30) is herein referred to as meeting point; and in this point or area a raised strip (21), e.g. each raised strip, mates with a mating strip (31), e.g. without direct contact.

A feeder (60) may deliver the absorbent material (100) to said first moving endless surface. Such as feeder (60) is capable of containing the absorbent material (100) and letting it flow to the supporting sheet (200) on said second moving endless surface, for example continuously. The feeder (60) may be a (e.g. stationary) hopper with a container portion, to hold the material, e.g. having a volume of at least 1000 cm$^3$, and it may have a guiding portion, e.g. a pipe-shapes portion, that guides the material from the container portion to the first moving endless surface.

Figure 2:
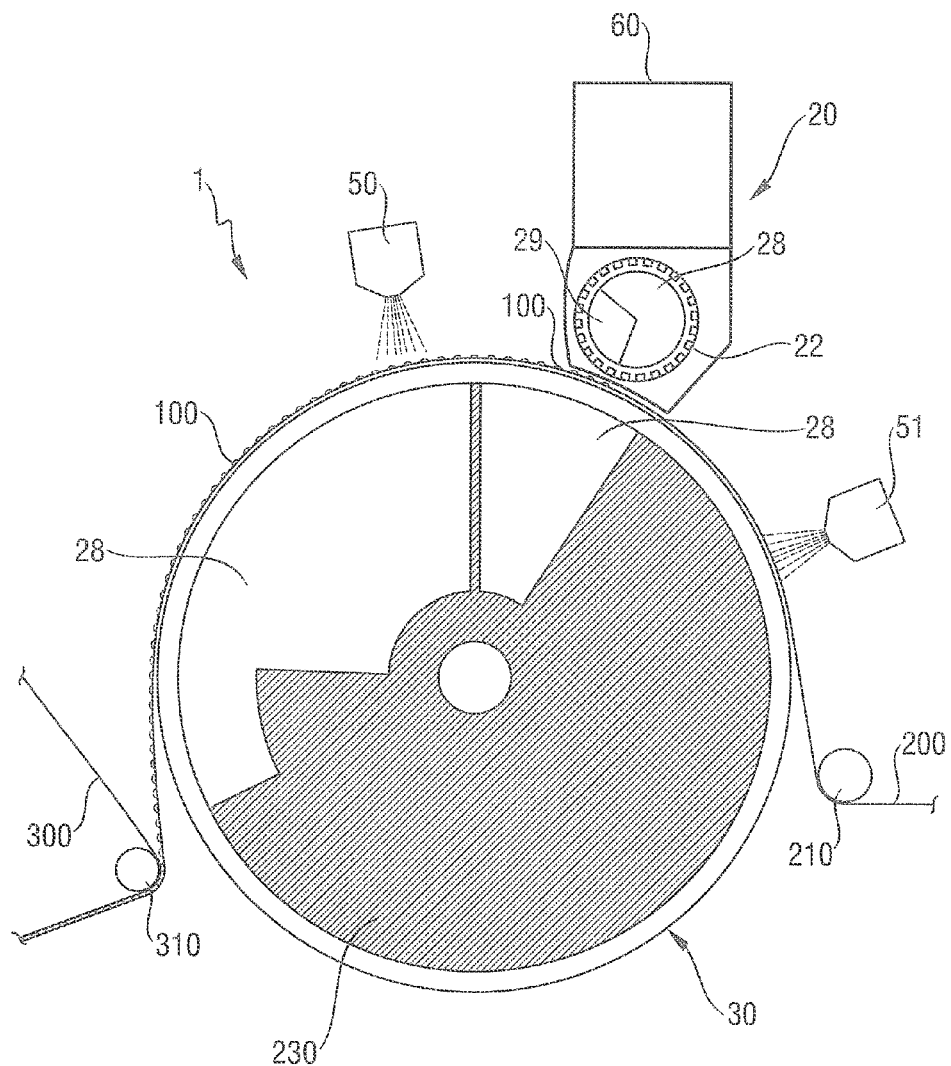
FIG. 2 is a side view of an apparatus (1) of the present disclosure, or used in the method of the invention.

The first moving endless surface (20) may be a rotating roll or drum, as for example shown in the FIGS. 2, 3 and 4. The radius of the first moving endless surface (20) may depend on what absorbent structure is produced, e.g. what size, and for example how many structures are produced per cycle of the first moving endless surface, e.g. print roll or drum. For example, the drum/print roll may have a radius of at least 40 mm, or of at least 50 mm; it may be for example up to 300 mm, or up to 200 mm. In some embodiments, the radius of the first moving surface is less than 50% of the radius of the second moving endless surface.

The first moving endless surface (20) may have any suitable width, but for example a width (for example in CD, hence perpendicular to MD) corresponding (substantially) to the width of the absorbent structure to be produced; this for example be at least 40 mm, or at least 60 mm, or for example up to 400 mm, or up to 200 mm.

Said first moving endless surface (20) may have one or more reservoirs with a certain volume for receiving said absorbent material (100) therein, and transporting it to and then depositing it on said supporting sheet (200) on a second moving endless surface.

Each reservoir (25) corresponds typically to an absorbent structure to be produced, as suitable for an absorbent article. The supporting sheet (200) may be a web material, so the method and apparatus (1) herein can thus serve to produce a web of such absorbent structures that are then subsequently separated into individual structures.

The reservoir (25) is at least partially air-permeable. It typically has an area that serves to receive said absorbent material, and this area is substantially in air-communication with a vacuum system, i.e. air permeable.

Figure 1B:
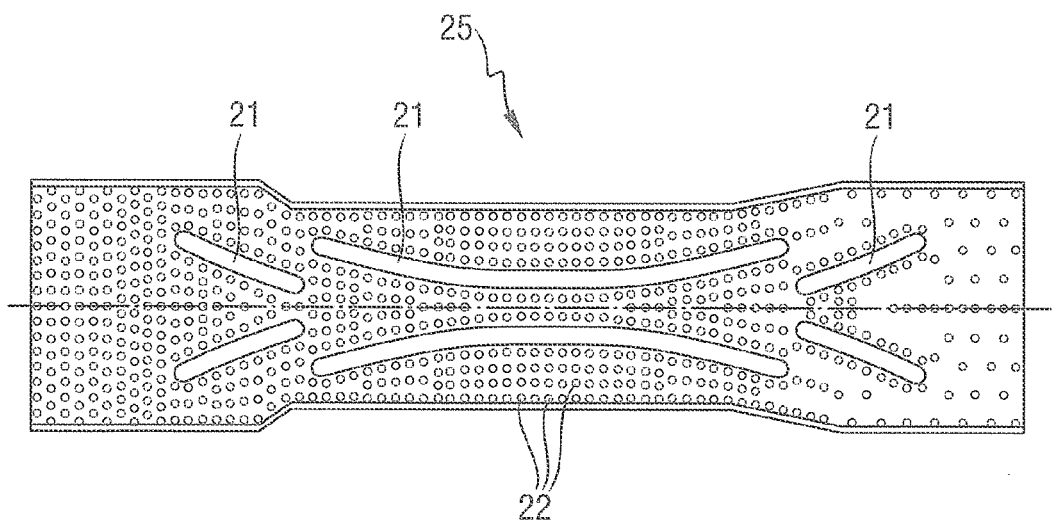
FIG. 1B is a top view of an alternative reservoir (25) of the first moving endless surface (20) herein.

As for example shown in FIGS. 1A and 1B and FIG. 3, the reservoir (25) has one or more raised strips (21) (that have no void volume) and that, when the first moving endless surface (20) moves (rotates) adjacent said second moving endless surface (30) with said supporting sheet (200) on said mating strips (31), said raised strips (21) mate substantially coincide (herein referred to as: mate) with said mating strips (31). Then, the absorbent material (100) is deposited selectively on the substrate material on the portions thereof that are not on said mating strips (31), to form an absorbent layer on a supporting sheet (200), having channels (strips) that are substantially free of absorbent material. A reservoir (25) has typically the same number of raised strips (21) as the number of mating strips (31) of the second moving endless surface.

Said strip(s) (21) may not be in air communication with a vacuum system that is in air communication with said first moving endless surface, i.e. the raised strips (21) may be air impermeable. They may have thereto have surfaces that have no apertures. The remaining area of the reservoir (25) that has void volume for receiving the absorbent material, thus excluding the raised strips (21), may be in air-communication with a vacuum system, e.g. having apertures in air-communication with a vacuum system.

The reservoir (25) has peripheral edges, and peripheral edge zones, including opposing longitudinal edges and edge zones, and a transverse front edge and front edge zone, and a transverse back edge and back edge zone. Each of said front and back edge zones, extending the complete transverse dimension, may for example have a longitudinal dimension of from about 5% to about 20%, or to 15%, or to 10% of the average longitudinal dimension of the reservoir. Each of said longitudinal edge zone may extend the length of the reservoir (25) and may have an average transverse dimension of for example from about 5% to about 20%, or typically to about 15% or to about 10% of the total average transverse dimension of the reservoir. In some embodiments herein, said raised strip(s) are not present in any of said edge zones.

The reservoir (25) may in addition, or alternatively, comprise a front region, back region and central region, therein between, as further described below. The central region may be for example the central ⅓ of the reservoir, extending the full transverse dimension. In some embodiment, the raised strips (21) are present only in the front region; alternatively, in some embodiments, the raised strips (21) are present in the central region only or at least; alternatively, in some embodiments, the raised strips (21) are present in the central region and front region and optionally in the back region. It may alternatively or in addition be preferred that one or more raised strips (21) are present in the central region and front region. To provide improved liquid transportation and more efficient absorbency by the whole absorbent structure, it may be preferred to have said raised strip(s) at least in the central region and optionally extending also at least in the front region.

In any such case, it may be preferred that none of the edge zones described above comprises such raised strips (21).

As for example shown in FIGS. 3 and 4, a raised strip (21) meets (and hence mates with) a mating strip (31) during the transfer of the absorbent material (100) herein, i.e. during absorbent material (100) transfer to said second moving endless surface, said raised strip (21) substantially overlaps said mating strip. This typically applies to each mating raised strip (21) and mating strip. In other words, each raised strip (21) typically has a corresponding mating strip. It should be understood that the raised strip (21) and mating strip (31) do not directly touch during the absorbent material (100) transfer (the supporting sheet (200) material is in between them). The supporting sheet (200) may or may not touch the raised strip(s).

The following is described for a raised strip, in relation to its corresponding mating strip, but may be, applicable to each raised strip.

A raised strip (21) and the corresponding mating strip (31) may have the same size and shaped and surface area, and be hence completely mating. It may be that a raised strip (21) has a surface area that is slightly more than the surface area of a corresponding mating strip. Hereby, the mating strip (31) and the corresponding raised strip (21) then typically still have substantially the same overall shape. Preferred length ratios and dimensions are herein described above and below.

In some embodiments, it may be preferred (in addition or as alternative of the above) that a mating strip (31) may have an average width W' that is less than the average width W of the raised strip, but in some embodiments, W' is not more than W, as further described above and below.

W is at typically least 5 mm, or for example at least 6 mm. or for example at least 7 mm or for example at least 8 mm, and for example less than 40 mm or less, or less 30 mm or less, or for example 20 mm or less.

A raised strip (21) extends typically at the most 80% or at the most 70% of the longitudinal dimension of the reservoir.

Thus, the average length of a raised strip (21) may be 80% or less of the average length of the reservoir, or for example at the most 70%.

The raised strips (21) are substantially longitudinally extending. They may be straight or for example curved, with a radius of curvature as describe herein, or angled, as described herein below.

The reservoir (25) may have for example at least two raised strips (21) on either side of the longitudinal axis of the reservoir, and being mirror images of one another. This is for example shown in FIG. 1A.

The reservoir (25) may also for example have 3 or 4, or for example 5 or for example 6 raised strips (21). Two or more thereof may be parallel to one another. The reservoir (25) may have for example 3, or 4, or 5, or 6 raised strips (21) that are at least present in the central region, and optionally extend in the front region and optionally in the back region; they may be parallel to one another and/or they may be such that those on one longitudinal side of the longitudinal axis of the reservoir (25) are mirror images of those that are on the opposite longitudinal side. This is for example shown in FIG. 1B.

The reservoir (25) may have for example two raised strips (21) in the front region, on either side of the longitudinal axis, and mirror images of one another therein; and two raised strips (21), extending in at least the central region, on either side of the longitudinal axis, and mirror images of one another therein; and optionally two raised strips (21) in the back region, on either side of the longitudinal axis, and mirror images of one another therein.

In some embodiments, there may be no raised strip (21) coinciding with the longitudinal axis of the reservoir, but only on either side thereof. This may help to ensure an absorbent structure formation into a U-shape during use, rather than a V-shape, which may be better for fit and/or absorbency.

In some embodiments, at least two raised strips (21) extend, and hence have an average length of, at least 50% of the average length of said reservoir. In some embodiments, there are at least an additional two raised strips (21) that have an average length that is less than 50% of the average length of the reservoir.

The raised strip's cross-section in the X-Z plane (X being transverse dimension; Z being height dimension) may be any form. It may have a square, rectangular, or hexagonal cross-section, for example. However, the top surface is typically flat, i.e. in the X-Y plane of the reservoir.

(Each of) said raised strip(s) herein is typically substantial longitudinally extending, which means that its longitudinal extension is more than its transverse extension. This includes raised strip(s) that are completely longitudinally extending and straight; it includes raised strip(s) under an angle with the longitudinal axis of the reservoir, provided said angle is at the most 30°; this may include raised strip(s) that may be slightly curved (as described herein below); this includes raised strip(s) that may be wavy; this includes raised strip(s) that may comprise an angle(s), provided said angle is at least 120°; and provided that any such raised strip(s) extend more in longitudinal dimension than in transverse dimension, e.g. that any such raised strip(s) extend at least 50% or at least 100% more in longitudinal dimension than in transverse dimension.

In some embodiments, one or more of the raised strips (21) may be slightly curved, for example having a single curvature, as for example shown in the Figures, having a curvature with a radius that is at least equal to the average transverse dimension of the reservoir; and/or having a curvature following for example the contour of the closest longitudinal side edge. In some embodiments it may be preferred that the raised strips (21) are concave, wherein the longitudinal centre of the strip is closer to the longitudinal-axis of the reservoir (25) than the end point(s), and wherein the radius of curvature is at least 1 time, or optionally at least 1.5 times the average transverse dimension of the reservoir.

In some embodiments, the reservoir (25) is, in addition to said raised strip (21) or strips, composed of multitude of grooves, extending substantially in longitudinal dimension, or a multitude of rows of cavities, extending substantially in longitudinal dimension, for receiving the absorbent material (100) therein, with therein between said raised strip(s).

In some embodiments herein, said raised strips (21) have a contour, and adjacent either longitudinal side thereof, there is at least one such first row or groove, and adjacent thereto a second row and/or or groove, and said second row and/or groove may have a total volume less than the total volume of said first row or groove. Thereby, directly adjacent a channel (in the absorbent structure herein) the absorbent material (100) may have a higher basis weight than in a further adjacent zone.

In some embodiments herein, neighboring grooves or rows may be separated from one another but the spacing distance (in transverse dimension) between neighboring cavities (22) of neighboring rows or between neighboring grooves is less than 5 mm, and typically 4 mm or less, or 3.5 mm or less, or for example 3 mm or less.

Such grooves and/or rows may during the absorbent material (100) transfer mate with (coincide with) the portions of the substrate material that are between the neighboring rods (36), if present, and as described below, that extend substantially in longitudinal dimension; and hence, the areas between neighboring grooves and/or rows may mate (coincide) during absorbent material (100) transfer with the portions (strips) of the supporting sheet (200) that are on said rods (36), if present, as described below.

The cavities (22) may have any dimensions and shape, including cubical, rectangular, cylindrical, semi-spherical, conical, or any other shape. This may be any suitable number of cavities, but for example at least 20 or at least 50.

The cavities (22) may be present as identical cavities (22) or they may vary in dimension(s) or shape. The exact pattern, dimensions etc. will depend on the required structure to be formed, but may for example also depend on the particle size of the absorbent material, process speed etc.

In some embodiments at least 30% of the surface area of the reservoir (25) of the first moving endless surface (20) comprises said cavities, optionally at least 40%; and optionally up to 60% or up to 55%.

The distance in longitudinal dimension between the centre point of a cavity (22) (said centre point being in the plane of the outer surface of the first moving endless surface) and the centre point of a neighboring cavity (22) (in a row of cavities (22)) may for example be at least 3 mm, or at least 4 mm, or at least 6 mm, or for example up to 40 mm or up to 30 mm or up to 20 mm. This may apply to all such distances between neighboring cavities (22) in longitudinal dimension, or this may be an average over all such distances.

The distance in transverse dimension between the centre point of a cavity (22) or groove (said centre point being in the plane of the outer surface of the first moving endless surface) and the centre point of a neighboring cavity (22) or groove (in a transverse line of cavities) may for example also be as above. In some embodiments, the shortest distance in transverse dimension between two neighboring cavities (22) of a line of cavities (22) or between neighboring grooves is 4.0 mm or less.

In some embodiments, the longitudinal dimension of a cavity (22) may be (on average over all cavities (22) and/or for each cavity; measured over the outer surface of the first moving endless surface) at least 1 mm, or at least 2 mm, or at least 4 mm, and for example at the most 20 mm or at the most 15 mm. The transverse dimension may be within the same ranges as above, or it may even be the same as the longitudinal dimensions for one or more or each cavity.

Said rows or grooves may extend substantially parallel to, and equally spaced from, one another and/or said lines may extend substantially parallel to, and equally spaced from, one another.

In some embodiments, two or more of the rows or grooves, or part thereof, may be in the form of the longitudinal side edges of the raised strip, to which they are adjacent (and hence typically parallel), e.g. having the same curvature, angle etc as described herein.

The reservoir, cavities (22) or grooves may have any suitable dept dimension, and it may depend for example on the height of the first moving endless surface (20) (e.g. radius), the thickness of the desired structure to be produced, the particle size of the material, etc. The maximum depth of a reservoir, cavities (22) or grooves and/or the average maximum depth (average over all maximum depths of all cavities (22) and/or grooves) may for example be at least 1 mm, or at least 1.5 mm, or for example 2 mm or more, and for example up to 20 mm, or up to 15 mm, or in some embodiment herein, up to 10 mm, or to 5 mm, or to 4 mm.

According to some embodiments herein, the cavities (22) may have a an average dimension in longitudinal dimension and in transverse dimension of from 2 to 8 mm or from 3 mm to 7 mm; and the cavities (22) may have a maximum depth and/or average maximum depth of for example from 1.5 mm to 4 mm.

A scraper or doctor blade may be used to remove excess absorbent material. Excess material may be removed from the reservoir (25) and recycled back to e.g. the hopper One possibility to hold the material in the reservoir (25) (or its grooves or cavities) may be a vacuum applied to the inner side of the first moving endless surface, e.g. print roll or drum, in combination with suction apertures in (the bottom) of the reservoir, or of the grooves, or of cavities (22) thereof, to thus apply the vacuum suction onto the absorbent material. The vacuum is for example released just before or at the meeting point. The vacuum may be any vacuum pressure such as for example at least 10 kPa, or at least 20 kPa.

The vacuum may be provided by providing one or a plurality of vacuum chambers (28) in said first moving endless surface (20) (e.g. in its interior), wherein said vacuum can be applied, reduced, increased, and released (disconnected), depending on the position thereof in the process/apparatus.

Additional air pressure may be applied to said absorbent material (100) close to or at the meeting point, by provision of an air chamber (29) to ensure that the material flows to the supporting sheet (200) on said second moving endless surface.

Second Moving Endless Surface (30)

The method and apparatus (1) herein deploy a second moving endless surface (30), moving, like the first moving endless surface, in a machine direction (MD). It has an outer shell with one or more forming receptacle (s) (33), for receiving thereon or therein the supporting sheet (200) (which may be a web material, as described herein below, or individual sheets that are placed on a receptacle (33)). The following is described for a single receptacle (33) but may apply to each receptacles (33) of the second moving endless surface's outer shell.

Each receptacle (33) corresponds typically to an absorbent structure to be produced, as suitable for an absorbent article. The supporting sheet (200) may be a web material, so the method and apparatus (1) herein can thus serve to produce a web of such absorbent structures that are then subsequently separated into individual structures.

The second moving endless surface (30) may have or be a rotating surface, such as a rotating, e.g. cylindrical, drum. It may be that the outer shell moves, e.g. rotates, around a stationary inner chamber, e.g. a so-called stator.

The outer shell and the receptacle (33) have an average transverse dimension, which may for example be the cross-machine (CD) dimension, and the receptacle (33) has an average longitudinal dimension perpendicular thereto, which may for example be the machine dimension.

The receptacle (33) is at least partially air-permeable. It typically has an area that serves to receive said absorbent material, and this area is substantially in air-communication with a vacuum system, i.e. air permeable.

The receptacle (33) has one or more, optionally at least 2, substantially mating strips (31), that substantially mate (coincide) with said raised portion (but without contacting these directly), herein referred to as mating strips (31). Said mating strip(s) may not be in air communication with said vacuum system, i.e. it may be air impermeable. They may have thereto e a surface in the plane of the receptacle (33) that has no apertures.

A receptacle (33) has typically the same number of mating strips (31) as the number of raised strips (21) of a reservoir (25) of the first moving endless surface.

A raised strip (21) coincides (and hence mates with) a mating strip (31) during the transfer of the absorbent material (100) herein, i.e. during absorbent material (100) transfer to said second moving endless surface, said raised strip (21) substantially overlaps said mating strip. This typically applies to each mating raised strip (21) and mating strip. In other words, each raised strip (21) typically has a corresponding mating strip. It should be understood that the raised strip (21) and mating strip (31) do not directly touch during the absorbent material (100) transfer (the supporting sheet (200) material is in between them). The supporting sheet (200) may or may not touch the raised strip(s) (21); typically it does not.

The receptacle (33) has peripheral edges, and peripheral edge zones, including opposing longitudinal edges and edge zones, and a transverse front edge and front edge zone, and a transverse back edge and back edge zone. Each of said front and back edge zones, extending the complete transverse dimension, may for example have a longitudinal dimension of from about 5% to about 20%, or to 15%, or to 10% of the average longitudinal dimension of the receptacle (33). Each of said longitudinal edge zone may extend the length and may have an average transverse dimension of for example from about 5% to about 20%, or typically to about 15% or to about 10% of the average transverse dimension of the receptacle (33). In some embodiments, the mating strips (31) is not present in any of the edge zones.

The receptacle (33) may in addition, or alternatively, comprise a front region, back region and central region, therein between, as further described below. The central region may be for example the central ⅓ of the receptacle (33), extending the full transverse dimension. In some embodiment, the mating strip(s) are present only in the front region; alternatively, in some embodiments, the mating strip(s) are present in the central region only or at least; alternatively, in some embodiments, the mating strip(s) are present in the central region and front region and optionally in the back region. It may alternatively or in addition be preferred that one or more mating strips (31) are present in the central region and front region. To provide improved liquid transportation and more efficient absorbency by the whole absorbent structure, it may be preferred to have said mating strip(s) at least in the central region and optionally extending also at least in the front region.

In any such case, it may be preferred that none of the edge zones described above comprises such mating strips (31).

The following is described for a mating strip, in relation to its corresponding raised strip, but may be, and optionally is, applicable to each mating strip (31) (and its corresponding raised strip).

A mating strip (31) and the corresponding raised strip (21) may have the same size and shaped and surface area, and be hence completely mating. It may be that a raised strip (21) has a surface area that is slightly more than the surface area of a corresponding mating strip. Hereby, the mating strip (31) and the corresponding raised strip (21) then typically still have substantially the same overall shape.

In some embodiments, it may be preferred that at least the average length of a mating strip (31) and the average length of a corresponding mating step are substantially the same, the difference for example being at the most 20%, or for example the raised strip (21) having an average length that is at the most 10% more than the average length of the corresponding mating strip. The average length L' of a mating strip (31) is hence from about 0.8×L to 1.2×L, or for example from 0.9×L to 1.1×L, or to 1×L, (L being the average length or the corresponding raised strip).

In some embodiments, it may be preferred (in addition or as alternative of the above) that a mating strip (31) may have an average width W' that is less than the average width W of the raised strip, but in some embodiments, W' is not more than W. Hence, W' is from 0.5×W to 1.2×W, or for example from 0.66×W, or for example from 0.8×W, to for example 1×W, or for example to 0.9 x W.

W' may for example be at least 2.5 mm, or for example at least 4 mm or for example at least 6 mm. W' may be less 20 mm or less, or less 15 mm or less, or for example 10 mm or less.

Thus in some embodiments, a raised strip (21) is completely overlapping a corresponding mating strip (31) during the absorbent material (100) transfer, but a mating strip (31) is not substantially overlapping a corresponding raised strip. This may help spreading of the deposited absorbent material (100) slightly on said supporting sheet (200), to ensure a more homogeneous deposition thereof on said supporting sheet (200).

Each mating strip (31) extends typically at the most 90% of the longitudinal dimension of the receptacle (33), or for example at the most 80% or at the most 70%.

Thus, the average length of a mating strip (31) may be 90% or less of the average length of the receptacle (33), or for example at the most 80% or at the most 70%.

The receptacle (33) may have for example at least two mating strips (31) on either side of the longitudinal axis of the receptacle (33), and being mirror images of one another. They may be straight or for example curved, with a radius of curvature as describe herein.

The receptacle (33) may also for example have 3 or 4, or for example 5 or for example 6 mating strips (31). Two or more thereof may be parallel to one another.

The receptacle (33) may have for example 3, or 4, or 5, or 6 mating strips (31) that are at least present in the central region, and optionally extend in the front region and optionally in the back region; they may be parallel to one another and/or they may be such that those on one longitudinal side of the longitudinal axis of the receptacle (33) are mirror images of those that are on the opposite longitudinal side.

The receptacle (33) may have for example two mating strips (31) in the front region, on either side of the longitudinal axis, and mirror images of one another therein; and two mating strips (31), extending in at least the central region, on either side of the longitudinal axis, and mirror images of one another therein; and optionally two mating strips (31) in the back region, on either side of the longitudinal axis, and mirror images of one another therein.

In some embodiments, there may be no mating strip (31) coinciding with the longitudinal axis of the receptacle (33), but only on either side thereof. This may help to ensure an absorbent structure formation into a U-shape during sue, rather than a V-shape, which may be better for fit and/or absorbency.

In some embodiments, at least two mating strips (31) extend, and hence have an average length (longitudinal dimension) of are at least 50% of the average length of said receptacle (33). In some embodiments, there are at least an additional two mating strips (31) that ahev an average length that is less than 50% of the average length of the receptacle (33).

The mating strip (31) cross-section in the X-Z plane may be any form. It may have a square, rectangular, or hexagonal cross-section, for example. However, the tops surface that supports the supporting sheet (200) is typically flat, i.e. in the X-Y plane of the receptacle (33).

(Each of) said mating strip(s) (31) herein is typically substantial longitudinal extending, which means that its longitudinal extension is more than its transverse extension. This includes mating strip(s) (31) that are completely longitudinally extending and straight; it includes mating strip(s) under an angle with the longitudinal axis of the reservoir, provided said angle is at the most 30°; this may include mating strip(s) that may be slightly curved (as described herein below); this includes mating strip(s) that may be wavy; this includes mating strip(s) that may comprise an angle(s), provided said angle is at least 120°; and provided that any such mating strip(s) extend more in longitudinal dimension than in transverse dimension, e.g. that any such mating strip(s) extend at least 50% or at least 100% more in longitudinal dimension than in transverse dimension.

In some embodiments, one or more of the mating strips (31) may be slightly curved, for example having a single curvature, having a curvature with a radius that is at least equal to the average transverse dimension of the reservoir; and/or having a curvature following for example the contour of the closest longitudinal side edge. In some embodiments it may be preferred that the mating strips (31) are concave, wherein the longitudinal centre of the strip is closer to the longitudinal-axis of the reservoir (25) than the end point(s), and wherein the radius of curvature is at least 1 time, or optionally at least 1.5 times the average transverse dimension of the reservoir.

The receptacle (33) area other than said mating strips (31) may for example be a mesh material that hence has apertures and is in air communication with said vacuum system (38), e.g. being air permeable.

The surface area of the receptacle (33), other than the mating strips (31), may alternatively comprise thin supports substantially in transverse, for supporting the supporting sheet (200), as for example shown in FIG. 3, i.e. typically having a maximum dimension in longitudinal direction which may be less than the average width dimension of the adjacent mating strip; and/or for example at the most 4 mm, or for example at the most 3 mm.

As for example shown in FIG. 4, the receptacle (33) may further comprise a multitude of substantially longitudinally extending rods (36), spaced apart from one another, and typically from a neighboring mating strip, in transverse direction. Such rods (36) may then partially form the most outer surface of said receptacle (33), so that the supporting sheet (200) is received and carried by said rods (36) and said mating strips (31).

Between rods (36), or between rods (36) and a neighboring mating strip, there is then a spacing where the supporting sheet (200) may not be supported directly by the receptacle (33)'s mating strips (31) or rods (36).

The receptacle (33) may comprise said rods (36) over substantially the whole length (longitudinal dimension) of the receptacle (33); or for example over the whole length except the front edge zone and/or back edge zone; or, in some embodiments herein, the rods (36) may be present only in said central region; in some embodiments, the rods (36) may be present in the front region and optionally the central region, but not the back region; in some embodiments, the rods (36) may be present in the back region and optionally the central region, but not the front region.

The receptacle (33) may comprise such rods (36) over the whole width (longitudinal-dimension) of said receptacle (33); or for example over the whole width except in said longitudinal edge zones.

In any of these embodiments, the zone(s) or region(s) not comprising said rods (36) is herein referred to as rod-free zone or rod-free region; in said rod-free region or rod-free zone the supporting sheet (200) is then deposited onto said mating strips (31) and optionally said inner grid (e.g. a mesh material) directly.

Said receptacle (33) may have in said region(s) or zone(s) that not comprising said rods (36) a higher friction than said rods (36). This can aid to ensure the supporting sheet (200) is pulled in between the rods (36), or rods (36) and mating strips (31), in the low friction zone, and less or not at all in the high friction zone. For example, the receptacle (33) can be made of a higher friction material (e.g. a material with a less even surface), or may be treated with an friction-increasing agents, in those zones or regions not comprising said rods (36); or for example said zones or regions with rods (36), or only said rods (36), can be made of a lower friction material, or treated with friction-reducing agent.

A rod (36), if present, is substantial longitudinally-extending, which means for the purpose of the invention the same as defined above for the mating strip.

The rod (36) may be any shape or form. It may have a square, rectangular, round, oval or hexagonal cross-section in CD, for example. Each rod has a top portion (which may be the top surface for, for example, rods (36) that have a square or rectangular cross-section) and an opposing bottom portion or surface. Said top portion or surface is then in contact with the supporting sheet (200); said bottom surface may be adjacent (e.g.: on) an, at least partially, air-permeable inner grid.

In some embodiments, it may be preferred that the rod is generally rectangular with optionally a triangular-shaped top portion.

The minimum distance between neighboring rods (36) or neighboring rods (36) and a mating strip (31) is for example (in transverse dimension) at least 2 mm, or at least 3 mm, or at least 5 mm, or for example at least 10 mm.

Two or more rods (36) may be parallel to one another, so that the spacing distance between parallel neighboring rods (36), in transverse dimension, is at least said 2 mm along substantially the whole length.

Thus, there may be a void volume between neighboring rods (36), or between a rod and a neighboring mating strip, and said void volume extends substantially in machine direction. This void volume can serve to receive the supporting sheet (200) therein, as an undulation, and then optionally said absorbent material (100) therein.

Each rod may have a maximum cross-machine dimension which may be at least 0.1 mm, optionally at least 0.3 mm, or at least 0.5 mm, and for example less than 4 mm, or less than 2 mm.

The receptacle (33) may for example have at least 2 such rods (36), or for example at least 4 such rods (36), or for example at least 5 or at least 7 such rods (36).

Said rods (36) may be straight in longitudinal direction and/or they may for example be parallel to a neighboring mating strip.

In some preferred embodiments, the supporting sheet (200) is deposited onto said mating strips (31) and optional rods (36) and it bends in between neighboring mating strips (31) and/or rods (36), e.g. due to the vacuum suction, to form thereby in said sheet undulations between neighboring rods (36) and/or mating strips (31), and crests supported on said rods (36)/mating strips (31) (on said top surface or top portion). (The inner grid may control/determine the size (height) of said undulations.)

The supporting sheet (200) is transferred from a transfer means, such a transfer roll (210), to said second moving endless surface (30) and deposited onto said outershell/receptacle(s) (33). It may be transported to the outershell and receptacle (33) thereof as a web, or as individual sheets. The supporting sheet (200) may be a nonwoven material, as further described herein.

Subsequently, said absorbent material (100) may be deposited onto said supporting sheet (200), on said receptacle (33), such that substantially no material is deposited on the portions of the supporting sheet (200) that are on the mating strips (31).

The absorbent material (100) may be deposited such that it is only present on the portions of the supporting sheet (200) (e.g. strips of supporting sheet (200)) that is present between neighboring rods (36) and/or mating strips (31), e.g. in said undulations. Thereto, specific first moving surface may be used that has the specific grooves or cavities (22) that mate with said undulations, and not with said rods (36) as described below may be used.

Alternatively, or in addition, the vacuum may be such that it pulls the absorbent material (100) to or towards the portions of the supporting sheet (200) present between neighboring rods (36) and/or mating strips (31), e.g. into said undulations. Substantially no absorbent material (100) may for example be present on the supporting sheet (200) present on said rods (36), (not on said mating strips (31), as set out herein above already), e.g. on said crests of said supporting sheet (200).

Alternatively, or in addition, absorbent material (100) deposited onto the portions of the supporting sheet (200) on said rods (36) (e.g. said crests) may be removed by means known in the art, such as a scraper or doctor blade.

Alternatively, or in addition, the supporting sheet (200) may comprise adhesive. For example said adhesive may be present on said portions of said supporting sheet (200) that are between neighboring rod and/or mating strips (31), e.g. said undulations. This may help to adhere the absorbent material (100) in such portions, e.g. on said undulations. The supporting sheet (200) may then, prior to addition of the absorbent material, comprise no adhesive applied on said portions supported by said rods (36) and/or mating strips (31), e.g. said crests, so that less or no absorbent material (100) adheres in said portions, e.g. crests.

In some embodiments, the second moving endless surface (30) may for example have a speed of at least 1000 part per minute and/or a speed of at least 4.5 m/s, or at least 6 m/s, or at least 8 m/s.

Absorbent material (100)

The absorbent material (100) herein is optionally a flowable material (in the dry state), such as a particulate material; it may be any material in particulate form, which includes particles, flakes, fibers, spheres, agglomerated particles and other forms known in the art.

The absorbent material (100) comprises superabsorbent polymer material (e.g. particles), optionally combined with cellulosic material (including for example cellulose, comminuted wood pulp in the form of fibers). In some embodiment, the absorbent material (100) may comprise at least 60%, or at least 70% by weight of superabsorbent polymer material, and at the most 40% or at the most 30% of cellulosic material. In some other embodiments, the absorbent layer comprises absorbent material (100) that consists substantially of absorbent polymer material, e.g. particles, e.g. less than 5% by weight (of the absorbent material) of cellulosic material is present; and said absorbent layer/absorbent structure, may be free of cellulosic material.

In some embodiments herein, the absorbent material, e.g. the particulate absorbent material, comprises at least, or consists essentially of or consists of, (particulate) superabsorbent polymer material, herein referred to as SAP, and also known as particulate absorbent gelling material, AGM. The particulate SAP herein may have a high sorption capacity, e.g. having a CRC of for example at least 20 g/g, or at 30 g/g. Upper limits may for example be up to 150 g/g, or up to 100 g/g.

The particulate SAP may have a good permeability for liquid, for example, having a SFC value of at least $10\times10^{-7}$ cm$^3$ s/g; or optionally at least $30\times10^{-7}$ cm$^3$.s/g, or at least $50\times10^{-7}$ cm$^3$s/g $10\times10^{-7}$ cm$^3$s/g, or possibly permeability SFC value of at least $100\times10^{-7}$ cm$^3$s/g, or at least a SFC of $120\times10^{-7}$ cm$^3$ sec/g. This SFC is a measure of permeability and an indication of porosity is provided by the saline flow conductivity of the gel bed as described in U.S. Pat. No. 5,562,646, (Goldman et al.) issued Oct. 8, 1996 (wherein however a 0.9% NaCl solution is used instead of Jayco solution). Upper limits may for example be up to 350 or up to 250 ($\times10^{-7}$ cm$^3$.s/g).

In some embodiments herein the polymers of said SAP are internally cross-linked and/or surface crosslinked polymers.

In some embodiments herein, the absorbent material (100) comprising or consisting of particles of polyacrylic acids/polyacrylate polymers, for example having a neutralization degree of from 60% to 90%, or about 75%, having for example sodium counter ions, as known in the art; they may be surface crosslinked and/or internally crosslinked polyacrylic acid/polyacrylate polymers.

In some embodiments herein, the absorbent material (100) is in the form of particles with, a mass medium particle size up to 2 mm, or between 50 microns and 2 mm or to 1 mm, or optionally from 100 or 200 or 300 or 400 or 500 μm, or to 1000 or to 800 or to 700 μm; as can for example be measured by the method set out in for example EP-A-0691133. In some embodiments of the invention, the material is in the form of particles whereof at least 80% by weight are particles of a size between 50 μm and 1200 μm and having a mass median particle size between any of the range combinations above. In addition, or in another embodiment of the invention, said particles are essentially spherical. In yet another or additional embodiment of the invention the absorbent material (100) has a relatively narrow range of particle sizes, e.g. with the majority (e.g. at least 80% or optionally at least 90% or even at least 95% by weight) of particles having a particle size between 50 μm and 1000 μm, optionally between 100 μm and 800 μm, and more optionally between 200 μm and 600 μm.

The absorbent material (100) herein may advantageously comprise less than 15% by weight of water, or less than 10%, or less than 8% or less than 5%. The water-content can be determined by the Edana test, number ERT 430.1-99 (February 1999) which involves drying the particulate material (100) at 105° Celsius for 3 hours and determining the moisture content by the weight loss of the particulate material (100) after drying.

The particulate SAP herein may be particles of SAP that are surface coated or surface treated (this not including surface-crosslinking, which may be an additional surface-treatment); such coatings and surface treatment steps are well known in the art, and include surface treatment with one or more inorganic powders, including silicates, phosphates, and coatings of polymeric material, including elastomeric polymeric materials, or film-forming polymeric materials.

Supporting Sheet (200)

The absorbent structure producible with the apparatus (1) and method of the invention comprises a supporting sheet (200), to receive the absorbent material. This supporting sheet (200) may be any individual sheet or web sheet material, in particular paper, films, wovens or nonwovens, or laminate of any of these.

In some embodiments herein, the supporting sheet (200) is a nonwoven, e.g. a nonwoven web, such as a carded nonwoven, spunbond nonwoven or meltblown nonwoven, and including nonwoven laminates of any of these.

The fibers may be of natural or man-made origin and may be staple or continuous filaments or be formed in situ. Commercially available fibers have diameters ranging typically from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). The fibers may be bicomponent fibers, for example having a sheet-core arrangement, e.g. with different polymers forming the sheet and the core. Nonwoven fabrics can be formed by many processes such as meltblowing, spunbonding, solvent spinning, electrospinning, and carding. The basis weight of nonwoven fabrics is usually expressed in grams per square meter (gsm).

The nonwoven herein may be made of hydrophilic fibers; "Hydrophilic" describes fibers or surfaces of fibers, which are wettable by aqueous fluids (e.g. aqueous body fluids) deposited on these fibers. Hydrophilicity and wettability are typically defined in terms of contact angle and the strike through time of the fluids, for example through a nonwoven fabric. This is discussed in detail in the American Chemical Society publication entitled "Contact angle, wettability and adhesion", edited by Robert F. Gould (Copyright 1964). A fiber or surface of a fiber is said to be wetted by a fluid (i.e. hydrophilic) when either the contact angle between the fluid and the fiber, or its surface, is less than 90°, or when the fluid tends to spread spontaneously across the surface of the fiber, both conditions are normally co-existing. Conversely, a fiber or surface of the fiber is considered to be hydrophobic if the contact angle is greater than 90° and the fluid does not spread spontaneously across the surface of the fiber.

The supporting sheet (200) herein may be air-permeable. Films useful herein may therefore comprise micro pores. Nonwovens herein may for example be air permeable. The supporting sheet (200) may have for example an air-permeability of from 40 or from 50, to 300 or to 200 $m^3/(m^2 \times min)$, as determined by EDANA method 140-1-99 (125 Pa, 38.3 $cm^2$). The supporting sheet (200) may alternatively have a lower air-permeability, e.g. being non-air-permeable, to for example be better detained on a moving surface comprising vacuum.

In preferred executions, the supporting sheet (200) is a nonwoven laminate material, a nonwoven laminate web, for example of the SMS or SMMS type.

In order to form easily said undulations, the supporting sheet (200) may have a basis weight that is less than 60 gsm, or for example than 50 gsm, for example from 5 gsm to 40 gsm, or to 30 gsm.

The supporting sheet (200) may have a transverse-extensibility or a longitudinal-extensibility, for example of more the 20%, or for example more than 100%, but for example not more than 200%.

In one of the embodiment herein, the supporting sheet (200) has a transverse dimension that is more than the transverse dimension of the part of the receptacle (33), e.g. at least 10%, or for example at 20% or at least 30%, and for example up to about 120%.

Adhesive Application Units (50; 51) and Method Steps.

The supporting sheet (200) may comprise and adhesive prior to transfer to said second moving endless surface. Thus, the apparatus (1) herein may comprise a (second) adhesive application unit (51) upstream from said second moving endless surface, and for example downstream from said supporting material transfer means, e.g. roll. The method herein may thus comprise such an adhesive application step.

This adhesive may be applied uniformly and/or continuously, to aid absorbent material (100) immobilization and then it may help to adhere the supporting sheet (200) to a further material that may overlay the absorbent layer, as described below. Alternatively, it may be applied in a pattern. It may be applied by spraying, or for example by selectively slot-coating; the apparatus (1) may thus comprise a slot-coater, with a pattern.

The adhesive may be applied on those portions of the supporting sheet (200) that are to receive to receive the absorbent material; then, it helps to immobilize the absorbent material (100) thereon (e.g. to ensure the absorbent material (100) will stay substantially as applied, with said channels, optionally not only during manufacturing, but also during storage and in use (at least during part of the use). Or, alternatively, only on those portions of the supporting sheet (200) that are to be on said mating strips (31); then it may help to adhere the supporting sheet (200) to a further material that may overlay the absorbent layer, as described below. It may be applied as substantially longitudinal stripes, for example.

In some embodiments, the apparatus (1) may comprise a unit to apply an adhesive to said supporting sheet (200) in a pattern, for example the pattern of the mating strips (31), and optionally of the rods (36), if present.

Any suitable adhesive can be used for this, for example so-called hotmelt adhesives used. For example, a sprayable hot melt adhesives, such as H.B. Fuller Co. (St. Paul, Minn.) Product No. HL-1620-B, can be used.

Alternatively, or in addition, it may be beneficial to apply a further immobilization adhesive to said absorbent structure produced by the apparatus (1) or method herein, e.g. to ensure the absorbent material (100) will stay substantially as applied, with said channels, optionally not only during manufacturing, but also during storage and in use (at least during part of the use). This immobilization adhesive may then for example be applied onto said absorbent layer just after application of said absorbent material (100) onto said supporting sheet (200).

The apparatus (1) herein may thus have a further (first) adhesive application unit (50), e.g. downstream from said second moving endless surface' meeting point. The method may have a corresponding method step This adhesive may be applied uniformly and/or homogeneously. This may be a thermoplastic adhesive material.

In accordance with certain embodiments, the thermoplastic adhesive material may comprise, in its entirety, a single thermoplastic polymer or a blend of thermoplastic polymers, having a softening point, as determined by the ASTM Method D-36-95 "Ring and Ball", in the range between 50° C. and 300° C., or alternatively the thermoplastic adhesive material may be a hot melt adhesive comprising at least one thermoplastic polymer in combination with other thermoplastic diluents such as tackifying resins, plasticizers and additives such as antioxidants. In certain embodiments, the thermoplastic polymer has typically a molecular weight (Mw) of more than 10,000 and a glass transition temperature (Tg) usually below room temperature or −6° C.>Tg <16° C. In certain embodiments, typical concentrations of the polymer in a hot melt are in the range of about 20 to about 40% by weight. In certain embodiments, thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins. In exemplary embodiments, the tackifying resin has typically a Mw below 5,000 and a Tg usually above room temperature, typical concentrations of the resin in a hot melt are in the range of about 30 to about 60%, and the plasticizer has a low Mw of typically less than 1,000 and a Tg below room temperature, with a typical concentration of about 0 to about 15%. In certain embodiments, the thermoplastic adhesive material is present in the form of fibers. In some embodiments, the fibers will have an average thickness of about 1 to about 50 micrometers or about 1 to about 35 micrometers and an average length of about 5 mm to about 50 mm or about 5 mm to about 30 mm.

Further Method Steps/Apparatus Units

The apparatus (1) and method herein may comprise the further step/unit, of applying a further supporting sheet (300) onto said absorbent structure, to enclose said absorbent material, as know in the art. This may be done such that a channel or each channel of a first absorbent structure corresponds with a channel of the second absorbent structure.

The apparatus (1) and method herein may alternatively or in addition comprise the apparatus (1) unit/method step of folding the supporting sheet (200) over the absorbent material (100) to enclose it thereby. It may comprise a sealing unit, sealing step to seal the two supporting sheet (200) or the folded supporting sheet (200) along the peripheral edges of the absorbent layer.

The absorbent structure may alternatively or in addition be combined with other layers, such as an acquisition layer, or topsheet and the apparatus (1) and method herein may comprise according steps/units.

The method or apparatus (1) herein may be to produce an absorbent core or structure that comprises two or more of the above described absorbent structures; for example two such layers, superposed on one another such that the absorbent material (100) of a first layer and the absorbent material (100) of the other second layer are adjacent one another and sandwiched between the supporting sheet (200) of the first layer and the supporting sheet (200; 300) of the second layer. The apparatus (1) herein may thus be a combination apparatus, comprising two or more, e.g. two, of the apparatuses described herein, to produce two or more, e.g. two, absorbent structures, and then comprising a combining unit to combine the absorbent structures. The method may comprise according method step(s).

The absorbent structure produced with the method/apparatus (1) of the invention herein may also be combined with an absorbent structure produced by a method/apparatus (1) other than of the present disclosure, said combination may be done as set out above.

The apparatus (1) may comprise a pressure means (70), such as a pressure roll, that can apply pressure onto the absorbent structure, and typically an absorbent structure wherein the absorbent material (100) is sandwiched between the supporting sheet (200) and a further material; the pressure may be applied onto said supporting sheet (200) or on any of the further material/layer that placed over the absorbent layer, as described above in this section. The method herein may then comprise a corresponding method step.

This pressure application may optionally be done to selectively apply pressure only onto the channels of the absorbent structure, e.g. on the portions of the supporting sheet (200) that correspond to the channels, and that thus not comprise (on the opposed surface) absorbent material, to avoid compaction of said absorbent material (100) itself.

Thus, the apparatus (1) may comprise a pressure means (70) that has a raised pressuring pattern (71) corresponding to said pattern of the raised strip(s) and/or of said mating strip(s), in some optionally corresponding to the pattern of the mating strip(s). The method may have an according method step.

Absorbent Articles

The apparatus (1) and method of the invention are for example useful to produce absorbent structures, or absorbent cores (i.e. said structures combined with a further material, described herein) suitable for absorbent articles.

Absorbent articles may include diapers, including fastenable diapers and (refastenable) training pants; adult incontinence undergarments (pads, diapers) feminine hygiene products (sanitary napkins, panty-liners), breast pads, care mats, bibs, wound dressing products, and the like. Ins some preferred embodiments, the absorbent article is a diaper, or adult incontinent product.

The absorbent article herein may comprise in addition to the absorbent structure or absorbent core, a topsheet and backsheet, and for example one or more side flaps or cuffs. The topsheet or cuffs or side flaps may comprise a skin care composition or lotion or powder, known in the art, panels, including those described in U.S. Pat. Nos. 5,607,760; 5,609,587; 5,635,191; 5,643,588.

Preferred absorbent articles herein comprise a topsheet, facing the wearer in use, for example a nonwoven sheet, and/or an apertured sheet, including apertured formed films, as known in the art, and a backsheet.

The backsheet may be liquid impervious, as known in the art. In preferred embodiments, the liquid impervious backsheet comprises a thin plastic film such as a thermoplastic film having a thickness of about 0.01 mm to about 0.05 mm. Suitable backsheet materials comprise typically breathable material, which permit vapors to escape from the diaper while still preventing exudates from passing through the backsheet. Suitable backsheet films include those manufactured by Tredegar Industries Inc. of Terre Haute, Ind. and sold under the trade names X15306, X10962 and X10964.

The backsheet, or any portion thereof, may be elastically extendable in one or more directions. The backsheet may be attached or joined to a topsheet, the absorbent structure or core described herein, or any other element of the diaper by any attachment means known in the art.

Diapers herein may comprise leg cuffs and/or barrier cuffs; the article then typically has a pair of opposing side flaps and/or leg and/or barrier cuffs, each of a pair being positioned adjacent one longitudinal side of the absorbent structure or core, and extending longitudinally along said structure or core, and typically being mirror images of one another in the longitudinal-axis of the article; if leg cuffs and barrier cuffs are present, then each leg cuffs is typically positioned outwardly from a barrier cuff. The cuffs may be extending longitudinally along at least 70% of the length of the article. The cuff(s) may have a free longitudinal edge that can be positioned out of the X-Y plane (longitudinal/transverse directions) of the article, i.e. in z-direction. The side flaps or cuffs of a pair may be mirror images of one another in the Y-axis (longitudinal axis) of the article. The cuffs may comprise elastic material.

The diapers herein may comprise a waistband, or for example a front waistband and back waist band, which may comprise elastic material.

The diaper may comprise side panels, or so-called ear panels. The diaper may comprise fastening means, to fasten the front and back, e.g. the front and back waistband. Preferred fastening systems comprise fastening tabs and landing zones, wherein the fastening tabs are attached or joined to the back region of the diaper and the landing zones are part of the front region of the diaper.

The absorbent article may also include a sub-layer disposed between the topsheet and the absorbent structure or core, capable of accepting, and distributing and/or immobilizing bodily exudates. Suitable sublayers include acquisition layers, surge layers and or fecal material storage layers, as known in the art. Suitable materials for use as the sub-layer may include large cell open foams, macro-porous compression resistant non woven highlofts, large size particulate forms of open and closed cell foams (macro and/or microporous), highloft non-wovens, polyolefin, polystyrene, polyurethane foams or particles, structures comprising a multiplicity of vertically oriented, optionally looped, strands of fibers, or optionally apertured formed films, as described above with respect to the genital coversheet. (As used herein, the term "microporous" refers to materials that are capable of transporting fluids by capillary action, but having a mean pore size of more than 50 microns. The term "macroporous" refers to materials having pores too large to effect capillary transport of fluid, generally having pores greater than about 0.5 mm (mean) in diameter and more specifically, having pores greater than about 1.0 mm (mean) in diameter, but typically less than 10 mm or even less than 6 mm (mean).

All patents and patent applications (including any patents which issue thereon) assigned to the Procter & Gamble Company referred to herein are hereby incorporated by reference to the extent that it is consistent herewith.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present disclosure. To the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for making an absorbent structure for an absorbent article, the absorbent structure comprising a supporting sheet and an absorbent layer on the supporting sheet, the absorbent layer comprising absorbent material and a channel that is substantially free of absorbent material, the apparatus comprising:
    a first moving endless surface having an absorbent layer-forming reservoir defining a void volume for receiving absorbent material therein, the reservoir comprising a substantially longitudinally extending raised strip;
    a feeder for feeding absorbent material to the first moving endless surface;
    a second moving endless surface having an outer shell including an air permeable receptacle for receiving a supporting sheet, the receptacle having a substantially longitudinally extending mating strip
    a vacuum system connected to the outer shell, the vacuum system adapted to facilitate retention of the supporting sheet and the absorbent material on the outer shell; and
    wherein, in a meeting point, the first moving endless surface and the second moving endless surface are adjacent and in close proximity of one another during transfer of absorbent material from the first moving endless surface to the second moving endless surface;
    wherein the mating strip is arranged to mate with the raised strip during transfer of the absorbent material; and
    a downstream pressure roll with a raised pressure pattern substantially corresponding to the mating strip, for contacting the supporting sheet in an area thereof corresponding to a channel.

2. The apparatus of claim 1, wherein the reservoir is formed by a multitude of cavities with a void volume for receiving the absorbent material therein.

3. The apparatus of claim 1, wherein the reservoir, excluding the raised strips, has apertures to be partially air permeable and wherein the first moving endless surface has a cylindrical surface with the reservoir rotatably moving around a stator comprising a vacuum chamber connected to the vacuum system; and wherein the second outershell is cylindrical rotatably moving around a stator comprising a vacuum chamber connected to the vacuum system.

4. The apparatus of claim 1, comprising:
    at least two mating strips the at least two mating strips are mirror images of one another with respect to a longitudinal axis of the receptacle; and
    at least two raised strips being mirror images of one another with respect to a longitudinal axis of the reservoir.

5. The apparatus of claim 1, wherein the receptacle further comprises a multitude of substantially longitudinally extending rods spaced apart from one another in transverse direction, and wherein top surfaces of the rods and the mating strips in the same plane of the receptacle.

6. The apparatus of claim 1, wherein the reservoir is formed by a plurality of cavities, and wherein cavities that are directly adjacent the raised strip have volumes that are greater than volumes of cavities that are not directly adjacent the raised strip.

7. The apparatus of claim 1, comprising an adhesive application unit positioned upstream from the meeting point.

8. The apparatus of claim 1, comprising downstream from the meeting point a unit to cover the absorbent layer with a further material, selected from a unit for folding the supporting sheet over the absorbent layer; a unit for applying a further supporting sheet; a unit for applying a further layered material, for example an acquisition material; a unit for combining the structure with a further absorbent structure.

\* \* \* \* \*